(12) United States Patent
Sumerin et al.

(10) Patent No.: US 12,391,778 B2
(45) Date of Patent: Aug. 19, 2025

(54) ZIEGLER-NATTA CATALYSTS FOR OLEFIN POLYMERIZATION

(71) Applicant: Borealis AG, Vienna (AT)

(72) Inventors: Victor Sumerin, Porvoo (FI); Georgy Kipiani, Porvoo (FI)

(73) Assignee: Borealis AG, Vienna (AT)

( * ) Notice: Subject to any disclaimer, the term of this patent is extended or adjusted under 35 U.S.C. 154(b) by 642 days.

(21) Appl. No.: 17/764,235

(22) PCT Filed: Oct. 1, 2020

(86) PCT No.: PCT/EP2020/077468
§ 371 (c)(1),
(2) Date: Mar. 28, 2022

(87) PCT Pub. No.: WO2021/064078
PCT Pub. Date: Apr. 8, 2021

(65) Prior Publication Data
US 2022/0380496 A1    Dec. 1, 2022

Related U.S. Application Data

(60) Provisional application No. 62/910,520, filed on Oct. 4, 2019.

(30) Foreign Application Priority Data

Oct. 4, 2019 (EP) ..................... 19201402

(51) Int. Cl.
| C08F 210/16 | (2006.01) |
| C07C 43/10 | (2006.01) |
| C07D 307/12 | (2006.01) |
| C07D 307/42 | (2006.01) |

(52) U.S. Cl.
CPC ............ C08F 210/16 (2013.01); C07C 43/10 (2013.01); C07D 307/12 (2013.01); C07D 307/42 (2013.01)

(58) Field of Classification Search
USPC .................................. 526/124.9, 129, 141
See application file for complete search history.

(56) References Cited

U.S. PATENT DOCUMENTS

| 4,071,674 A | 1/1978 | Iwakuni et al. |
| 6,683,017 B2 | 1/2004 | Gao et al. |
| 9,034,784 B2 * | 5/2015 | Standaert ............... C08F 10/06 526/213 |
| 2014/0148566 A1 | 5/2014 | Denkwitz et al. |

FOREIGN PATENT DOCUMENTS

| CN | 106928380 A | 7/2017 | |
| CN | 107129547 A | 9/2017 | |
| CN | 107344976 A | 11/2017 | |
| EP | 373999 A1 | 6/1990 | |
| EP | 0376936 A2 | 7/1990 | |
| EP | 0424049 A2 | 4/1991 | |
| EP | 0428054 A1 | 5/1991 | |
| EP | 0614467 A1 | 9/1994 | |
| EP | 633270 A1 | 1/1995 | |
| EP | 0655073 A1 | 5/1995 | |
| EP | 0688794 A1 | 12/1995 | |
| EP | 0361494 B1 * | 2/1996 | ............. C08F 4/654 |
| EP | 0810235 A2 | 12/1997 | |
| EP | 3083719 A1 | 10/2016 | |
| JP | H07145098 A | 6/1995 | |
| JP | 2003261614 A | 9/2003 | |
| JP | 2003321511 A | 11/2003 | |
| JP | 200616607 A | 1/2006 | |
| JP | 2016513167 A | 5/2016 | |
| JP | 2022549936 A | 11/2022 | |
| JP | 2022549937 A | 11/2022 | |
| JP | 2022550764 A | 12/2022 | |
| WO | 9212182 A1 | 7/1992 | |
| WO | 9618662 A1 | 6/1996 | |
| WO | 9951646 A1 | 10/1999 | |
| WO | 0155230 A1 | 8/2001 | |
| WO | 2003106510 | 12/2003 | |
| WO | 2003106514 | 12/2003 | |
| WO | 2004055065 A1 | 7/2004 | |
| WO | 2005118655 A1 | 12/2005 | |
| WO | 2006063771 A1 | 6/2006 | |
| WO | 2007051607 A1 | 5/2007 | |
| WO | 2007096255 A1 | 8/2007 | |

(Continued)

OTHER PUBLICATIONS

Machine-generated English language translation of CN107344976A, 26 pages, retrieved from Espacenet on Nov. 25, 2024. (Year: 2017).*
Machine-generated English language translation of JP2003261614A, 37 pages, retrieved from Espacenet on Nov. 25, 2024. (Year: 2003).*
Machine-generated English language translation of JP2003321511A, 21 pages, retrieved from Espacenet on Nov. 25, 2024. (Year: 2003).*
International Search Report for PCT/EP2020/077468 mailed Dec. 2, 2020, 13 pages.
Ville Nissinen, "The roles of multidentate ether and amine electron donors in the crystal structure formation of magnesium chloride supports", Department of Chemistry, University of Easter Finland, Jun. 28, 2017, 56 pages.

(Continued)

Primary Examiner — Fred M Teskin
(74) Attorney, Agent, or Firm — Lowenstein Sandler LLP

(57) ABSTRACT

The present invention relates to optionally substituted 1,3-dimethoxypropanes and 3-methoxypropylamines, and more particularly to their use as internal donors in Ziegler-Natta catalysts to obtain polymers with desirable properties. The present disclosure further concerns Ziegler-Natta catalyst components comprising said optionally substituted 1,3-dimethoxypropanes and 3-methoxypropylamines, and Ziegler-Natta catalysts for olefin polymerization comprising said Ziegler-Natta catalyst components, as well as a method for preparing the same and their use in providing polyolefins.

17 Claims, 2 Drawing Sheets

(56) References Cited

FOREIGN PATENT DOCUMENTS

Figure 1:
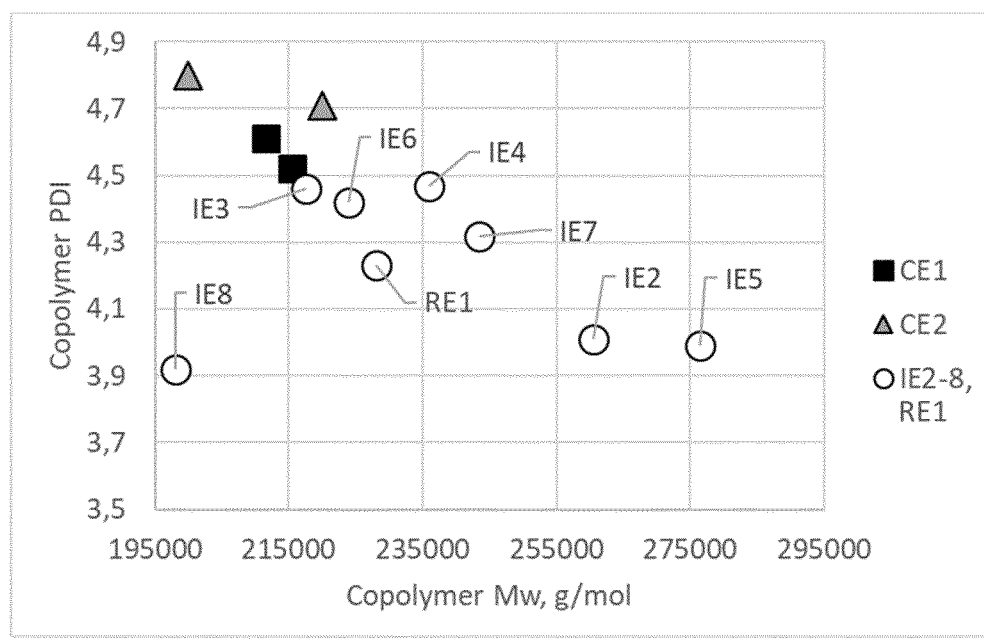

| WO | 2007147715 A1 | 12/2007 |
| WO | 2013098139 A1 | 7/2013 |
| WO | 2014004396 A1 | 1/2014 |
| WO | 2014096296 A1 | 6/2014 |
| WO | 2014096297 A1 | 6/2014 |
| WO | 2015091983 A1 | 6/2015 |
| WO | 2016097193 A1 | 6/2016 |
| WO | 2016124676 A1 | 8/2016 |

OTHER PUBLICATIONS

English Translation of Notice of Allowance for Japanese Patent Application No. 2022-519621, dated Sep. 5, 2023, 4 pages.
Office Action with English translation for Chinese Patent Application No. 202080068081.1 mailed Mar. 16, 2023, 43 pages.
Office Action for European Patent Application No. 20780719.9 dated Jun. 11, 2025, 7 pages.
Ferraro et al. "Advances in Ziegler-Natta Catalysts for Polypropylene", Kinetics and Catalysis, 2006, vol. 47, No. 2, 10 pages.
Barino et al. "Modeling of Isospecific Ti sites in MgCl2 Supported Heterogeneous Ziegler-Natta Catalysts", Macromol. Theory Simul. 7, 13 pages.

\* cited by examiner

ZIEGLER-NATTA CATALYSTS FOR OLEFIN POLYMERIZATION

CROSS-REFERENCE TO RELATED APPLICATION(S)

The present application is a national stage entry under 35 U.S.C. § 371 of International Application No. PCT/EP2020/077468, filed on Oct. 1, 2020, which claims priority to European Patent Application No. 19201402.5, filed on Oct. 4, 2019 and U.S. Provisional Application No. 62/910,520, filed on Oct. 4, 2019. The contents of these applications are hereby incorporated by reference in their entirety.

FIELD OF THE DISCLOSURE

The present invention relates to optionally substituted 1,3-dimethoxypropanes, and more particularly to the use of 1,3-dimethoxypropanes and 3-methoxypropylamines as internal donors in Ziegler-Natta catalysts to obtain polymers with desirable properties, in particular regarding molecular weight distribution (MWD) and chemical composition distribution (CCD). The present disclosure further concerns Ziegler-Natta catalyst components comprising said optionally substituted 1,3-dimethoxypropanes and 3-methoxypropylamines and Ziegler-Natta catalysts for olefin polymerization comprising said Ziegler-Natta catalyst components, as well as a method for preparing the same and their use in providing polyolefins.

BACKGROUND OF THE DISCLOSURE

Ziegler-Natta (ZN) type polyolefin catalysts are well known in the field of producing polyolefins, such as ethylene (co)polymers. Generally, the catalysts comprise at least a catalyst component formed from a transition metal compound of Group 4 to 6 of the Periodic Table (IUPAC, Nomenclature of Inorganic Chemistry, 2005), a metal compound of Group 1 to 3 of the Periodic Table (IUPAC), optionally a compound of Group 13 element of the Periodic Table (IUPAC), and optionally an internal electron donor. A ZN catalyst may also comprise further catalyst component(s), such as a cocatalyst and optionally an external electron donor.

Internal electron donor and internal donor have the same meaning and are interchangeable in this application. The same applies to an external electron donor and an external donor, respectively.

The catalyst composition used for the production of polyolefins, such as ethylene (co)polymers, determines i.a. the properties of the polymers. Thus, the catalyst composition allows for "tailoring" the properties of the produced polymers.

EP633270 A1 discloses the use of 1,3-diethers as external electron donors for the (co)polymerization of ethylene.

EP373999 A1 discloses a method for controlling the molecular weight distribution (MWD) of polyethylene homopolymers and copolymers using a Ziegler-Natta catalyst comprising an external electron donor selected from monoethers (e.g. tetrahydrofuran). It is suggested to add the monoether to the catalytic component in the presence of the cocatalyst, whereas it is strongly discouraged to contact the monoether and the catalytic component in the absence of the cocatalyst.

WO2007051607 A1 discloses another possibility of tailoring the properties of a multimodal ethylene polymer. An alkyl ether type internal electron donor, preferably tetrahydrofuran, is used to modify the Ziegler-Natta catalyst component and to influence the molecular weight distribution (MWD) of a higher molecular weight (HMW) component.

WO2007096255A1 discloses a solid catalyst component for the (co)polymerization of ethylene, which comprises Ti, Mg, halogen and an internal electron donor compound belonging to 1,2-diethers.

WO2003106514A2 discloses a process for the preparation of ethylene copolymers, carried out in presence of a catalyst comprising a product obtained by contacting (i) a solid catalyst component comprising Mg, Ti, halogen and a 1,3-diether of formula $(ROCH_2)_2C(R_1)R_2$, where R is a $C_1$-$C_{10}$ hydrocarbyl group, $R_1$ is methyl or ethyl, optionally containing a heteroatom and $R_2$ is a $C_4$-$C_{12}$ linear alkyl group, optionally containing a heteroatom, and (ii) an organo-aluminium compound.

WO2007147715 A1 discloses a catalyst component for the polymerization of olefins, which is obtained by a specific process, comprising Mg, Ti, halogen and 1,3-diethers as internal electron donors. The catalyst with 9,9-bis(methoxymethyl)fluorene as an internal electron donor is used for propylene polymerization.

WO2004055065 A1 discloses a solid catalyst component which comprises Ti, Mg, halogen and an electron donor in specific molar ratios for the preparation of copolymers of ethylene with α-olefins, where said α-olefins are homogeneously distributed along the polymer chains. The electron donor is preferably ether, such as tetrahydrofuran. Said catalyst component is used in polymerization processes together with an alkylaluminium compound and optionally with external electron donor. The optional external electron donor is said to be equal to or different from the electron donor used in catalyst component.

EP0376936 A2 discloses a $MgCl_2$-supported Ziegler-Natta catalyst, where spray-dried $MgCl_2$/alcohol carrier material is treated with a compound of group IA to IIIA (Groups 1, 2 and 13 of the Periodic Table according to IUPAC, Nomenclature of Inorganic Chemistry, 2005) then titanated with a titanium compound, optionally in the presence of internal electron donor. The optional internal donor compound (THF or di-isobutyl phthalate are given in those examples where internal electron was used) is added together with $TiCl_4$ or after addition of $TiCl_4$. However, the activity of the donor-modified catalysts of EP0376936 A2 was much lower than the original catalyst without the donor. Moreover, during the donor treatment step, a 10 wt % solution of triethylaluminium and a number of catalyst hydrocarbon washes were used, which resulted in a large amount of organic solvent waste.

WO2014004396 A1 discloses a catalyst component, where bi-heterocyclic compounds are used as internal electron donors. The catalyst component is used in propylene polymerization.

WO2014096296 A1 discloses a supported Ziegler-Natta catalyst component comprising an internal donor selected from bi-(oxygen-containing ring) compounds and use of such a catalyst component for preparing a catalyst system used in the polymerization of ethylene for producing high molecular weight polyethylene.

WO2013098139 A1 discloses a particulate Group 2 metal/transition metal olefin polymerization catalyst component, which is obtained by a specific process, comprising 1,3-diether compound as internal donor and the use of such a catalyst component for preparing a catalyst used in the polymerization of olefins, particularly propylene polymerization.

WO2016097193 A1 discloses a solid MgCl$_2$-based Ziegler-Natta catalyst component prepared by pre-treating a MgCl$_2$*-mROH adduct with a compound of Group 13 element and an internal organic compound being a bicyclic ether and further treated with a compound of Group 4 to 6 transition metal for producing polyolefins. Further disclosed is a preparation of said catalyst component, as well as a Ziegler-Natta catalyst comprising said solid catalyst component, a compound of a Group 13 element as cocatalyst and optionally external additives.

Although much development work in Ziegler-Natta catalyst preparation has been accomplished, there is still room for further improvement. Moreover, nowadays health, safety and environment policies are an important factor in the production of catalysts and further polymers. In other words, polymers must fulfill the strict health and environmental requirements of certain national and international institutions. One class of substances considered as potential harmful compounds is phthalates, which have been commonly used as internal electron donors in Ziegler-Natta-type catalysts. In addition, tetrahydrofuran has been classified as a hazardous substance.

For these reasons, it is still desirable to find further internal donors for use in Ziegler-Natta catalysts which do not include phthalates and/or tetrahydrofuran and which provide desired polymer properties, e.g. high molecular weight and/or narrow MWD and/or improved CCD. Further, from a commercial point of view, such catalysts should exhibit a reproducible morphology, composition and performance.

There is also a need to find a catalyst which is able to produce copolymers with wider melt flow rate (MFR) and density windows, such that there is the possibility to produce high molecular weight copolymers with narrow MWD (molecular weight distribution) and high comonomer content combined with low melting temperature.

Finally, the catalyst should demonstrate productivity on a level that makes it viable in commercial polymerization processes while producing polymers with a broad range of molecular weight.

Based on the teachings of prior art, it appears that donor modification might result in the improvement of some properties. However, very often these improvements are achieved at the expense of catalyst activity and comonomer response. In particular, MgCl$_2$-based catalysts prepared by precipitation methods are typically sensitive towards changes in preparation conditions.

BRIEF DESCRIPTION OF THE DISCLOSURE

An object of the present invention is to provide internal donors and, in particular, a Ziegler-Natta catalyst component comprising said internal donor, which overcomes the above disadvantages, is environmentally sustainable and supports the preparation of ethylene (co)polymers with a desirable molecular weight, molecular weight distribution (MWD) and chemical composition distribution (CCD).

The object of the present invention is achieved by use of compounds of formula (I) as internal donors, a Ziegler-Natta catalyst component comprising said internal donors, a Ziegler-Natta catalyst comprising the same, and use thereof in olefin polymerization, which are characterized by what is stated in the independent claims. Preferred embodiments of the invention are covered by the dependent claims.

DETAILED DESCRIPTION OF THE DISCLOSURE

Surprisingly, it has now been found that the use of compounds of formula (I) as discussed herein and hereafter in Ziegler-Natta catalyst provides excellent activity—hydrogen response balance when utilized in (co)polymerization of ethylene. Additionally, their use provides ethylene (co)polymers with desired molecular weight, molecular weight distribution (MWD) and chemical composition distribution (CCD).

Internal Donor (i)

Accordingly provided herein is the use of a compound of formula (I) as an internal donor in a Ziegler-Natta catalyst, especially for ethylene (co)polymerization, in particular for producing ethylene (co)polymer in a multi-stage process,

(I)

wherein
$X_1$ and $X_2$ are each independently selected from O and N($R_5$);
$R_1$ is selected from a group consisting of H, $C_{1-3}$-alkyl, and oxygen-containing heterocyclic ring; and
$R_2$ is selected from H and methyl, with the provisio that only one of $R_1$ and $R_2$ may be H;
$R_3$ and $R_4$ are independently selected from $C_{1-4}$-alkyl,
$R_5$ is selected from a group consisting of H, a linear, branched or cyclic $C_{1-8}$-alkyl group.

Preferably, $R_1$ is selected from a group consisting of H, methyl, tetrahydrofuryl and furyl. More preferably, $R_1$ is selected from a group consisting of H, methyl, 2-tetrahydrofuryl and 2-furyl.

Preferably $R_3$ and $R_4$ are independently selected from $C_{1-2}$-alkyl, more preferably $R_3$ and $R_4$ are methyl.

Preferably $R_5$ is selected from a group consisting of H, a linear or branched $C_{1-4}$-alkyl group, more preferably $R_5$ is methyl.

Preferred embodiments of the use of the present internal donor are described in the dependent claims, as well as in the following description.

In a first example, the compound of formula (I) is selected from compounds of formula (I-a)

(I-a)

wherein
$R_1$ is selected from a group consisting of H, $C_{1-3}$-alkyl, and oxygen-containing heterocyclic ring; and
$R_2$ is selected from H and methyl, with the provisio that only one of $R_1$ and $R_2$ may be H.

Preferably, $R_1$ is selected from a group consisting of H, methyl, tetrahydrofuryl and furyl. More preferably, $R_1$ is selected from a group consisting of H, methyl, 2-tetrahydrofuryl and 2-furyl.

In a second example, the compound of formula (I) is selected from compounds of formula (I-b)

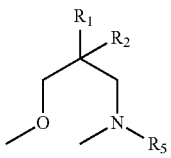

(I-b)

wherein
R₁ is selected from a group consisting of H, $C_{1-3}$-alkyl, and oxygen-containing heterocyclic ring;
R₂ is selected from H and methyl; and
R₅ is selected from a group consisting of H, a linear, branched or cyclic $C_{1-8}$-alkyl group.

Preferably, R₁ is selected from a group consisting of H, methyl, tetrahydrofuryl and furyl. More preferably, R₁ is selected from a group consisting of H, methyl, 2-tetrahydrofuryl and 2-furyl. Even more preferably, R₁ is H.

Preferably, R₅ is selected from a group consisting of H, a linear or branched $C_{1-3}$-alkyl, more preferably R₅ is methyl.

The term "oxygen-containing heterocyclic ring" refers to a cyclic structure containing an oxygen as part of the ring with 4 to 7 ring atoms, wherein the other ring atoms are preferably carbon atoms. The oxygen-containing heterocyclic ring is preferably a 5- to 6-membered ring comprising one oxygen atom as a member of the ring. The oxygen-containing heterocyclic ring may be saturated, partially unsaturated, unsaturated or aromatic. Preferably, the oxygen-containing heterocyclic ring is unsubstituted. In particular, the oxygen-containing heterocyclic ring is selected from a group consisting of tetrahydrofuryl and furyl, in particular from a group consisting of 2-tetrahydrofuryl and 2-furyl.

Further provided herein are novel compounds of formula (I), having formula (I-c)

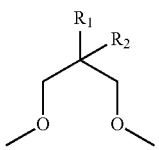

(I-c)

wherein
R₁ is selected from a group consisting of tetrahydrofuryl and furyl; and
R₂ is selected from H and methyl.

Preferably, R₁ is selected from a group consisting of 2-tetrahydrofuryl and 2-furyl.

In a particular example the compound of formula (I) is selected from a group consisting of 1,3-dimethoxy-2-methylpropane, 2,2-dimethyl-1,3-dimethoxypropane, 2-(1,3-dimethoxypropan-2-yl)tetrahydrofuran, 2-(1,3-dimethoxypropan-2-yl)furan, 2-(1,3-dimethoxy-2-methylpropan-2-yl)tetrahydrofuran, 2-(1,3-dimethoxy-2-methylpropan-2-yl)furan, and 3-methoxy-N,N-dimethylpropan-1-amine. In a further particular example, the compound of formula (I) is selected from a group consisting of 1,3-dimethoxy-2-methylpropane, 2,2-dimethyl-1,3-di methoxypropane, 2-(1,3-di methoxypropan-2-yl)tetrahydrofuran, 2-(1,3-dimethoxypropan-2-yl)furan, 2-(1,3-dimethoxy-2-methylpropan-2-yl)tetrahydrofuran, and 2-(1,3-dimethoxy-2-methylpropan-2-yl)furan.

It has been surprisingly found that by using the present internal donor of formula (I) in a Ziegler-Natta catalyst, especially for ethylene (co)polymerization, in particular for producing ethylene (co)polymer in a multi-stage process, it is possible to produce multimodal polyethylene having desirable molecular weight, molecular weight distribution (MWD) and chemical composition distribution (CCD).

The improvements, such as the increase in molecular weight and/or the narrowing of MWD, are not made at the expense of the productivity of the catalyst. Instead, productivity remains at an acceptably high level. Benefits are especially evident if the inventive internal donor is used in a multi-stage polymerization process comprising at least two stages, and more specifically in a multi-stage process, where at least one stage is carried out in gas phase.

(A) Ziegler-Natta Catalyst Component

Provided herein is a Ziegler-Natta catalyst component for olefin polymerization, especially for ethylene (co)polymerization, in particular for producing ethylene (co)polymer in a multi-stage process, comprising an internal donor selected from compounds of formula (I)

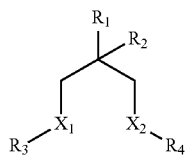

(I)

wherein
X₁ and X₂ are each independently selected from O and N(R₅);
R₁ is selected from a group consisting of H, $C_{1-3}$-alkyl, and oxygen-containing heterocyclic ring; and
R₂ is selected from H and methyl, with the provisio that only one of R₁ and R₂ may be H;
R₃ and R₄ are independently selected from $C_{1-4}$-alkyl,
R₅ is selected from a group consisting of H, a linear, branched or cyclic $C_{1-8}$-alkyl group.

Preferably, R₁ is selected from a group consisting of H, methyl, tetrahydrofuryl and furyl. More preferably, R₁ is selected from a group consisting of H, methyl, 2-tetrahydrofuryl and 2-furyl.

Preferably R₃ and R₄ are independently selected from $C_{1-2}$-alkyl, more preferably R₃ and R₄ are methyl.

Preferably, R₅ is selected from a group consisting of H, a linear or branched $C_{1-3}$-alkyl, more preferably R₅ is methyl.

Preferred embodiments of the present Ziegler-Natta catalyst component are described in the dependent claims as well as in the following description.

In a first example of the Ziegler-Natta catalyst component, the compound of formula (I) is selected from compounds of formula (I-a)

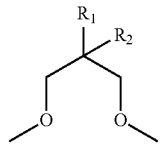

(I-a)

wherein
R₁ is selected from a group consisting of H, $C_{1-3}$-alkyl, and oxygen-containing heterocyclic ring; and $R_2$ is selected from H and methyl, with the proviso that only one of $R_1$ and $R_2$ may be H.

Preferably, $R_1$ is selected from a group consisting of H, methyl, tetrahydrofuryl and furyl. More preferably, $R_1$ is selected from a group consisting of H, methyl, 2-tetrahydrofuryl and 2-furyl.

In a second example of the Ziegler-Natta catalyst component, the compound of formula (I) is selected from compounds of formula (I-b)

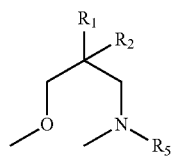

(I-b)

wherein
$R_1$ is selected from a group consisting of H, $C_{1-3}$-alkyl, and oxygen-containing heterocyclic ring;
$R_2$ is selected from H and methyl; and
$R_5$ is selected from a group consisting of H, a linear or branched or cyclic $C_{1-8}$-alkyl group. Preferably, $R_1$ is selected from a group consisting of H, methyl, tetrahydrofuryl and furyl. More preferably, $R_1$ is selected from a group consisting of H, methyl, 2-tetrahydrofuryl and 2-furyl. Even more preferably, $R_1$ is H.

Preferably $R_5$ is selected from a group consisting of H, a linear or branched $C_{1-3}$-alkyl, more preferably $R_5$ is methyl.

In a particular example, the compound of formula (I) is selected from a group consisting of 1,3-dimethoxy-2-methylpropane, 2,2-dimethyl-1,3-dimethoxypropane, 2-(1,3-dimethoxypropan-2-yl)tetrahydrofuran, 2-(1,3-dimethoxypropan-2-yl)furan, 2-(1,3-dimethoxy-2-methylpropan-2-yl)tetrahydrofuran, 2-(1,3-dimethoxy-2-methylpropan-2-yl)furan, and 3-methoxy-N,N-dimethylpropan-1-amine. In a further particular example, the compound of formula (I) is selected from a group consisting of 1,3-dimethoxy-2-methylpropane, 2,2-dimethyl-1,3-dimethoxypropane, 2-(1,3-dimethoxypropan-2-yl)tetrahydrofuran, 2-(1,3-dimethoxypropan-2-yl)furan, 2-(1,3-dimethoxy-2-methylpropan-2-yl)tetrahydrofuran, and 2-(1,3-dimethoxy-2-methylpropan-2-yl)furan.

The term "Ziegler-Natta catalyst component" as used herein and hereafter refers to a catalyst component, also called a procatalyst, of a Ziegler-Natta catalyst. Ziegler-Natta catalyst component of the present invention comprises at least a transition metal compound and an internal donor. In particular, it refers to a catalyst component formed from (ii) a compound of a transition metal of Group 4 to 6 of the Periodic Table (IUPAC, Nomenclature of Inorganic Chemistry, 2005), (iii) a compound of a metal of Group 1 to 3 of the Periodic Table (IUPAC, 2005), (iv) optionally a compound of an element of Group 13 or 14 of the Periodic Table (IUPAC, 2005), and (i) an internal donor.

Internal Donor (i)

The term "internal donor", also known as "internal electron donor", as used herein and hereafter refers to a compound being part of the Ziegler-Natta catalyst component, i.e. added during the synthesis of the Ziegler-Natta catalyst component and typically acting as an electron donor in the Ziegler-Natta catalyst system.

The internal donor is a part of the Ziegler-Natta catalyst component and is added to said Ziegler-Natta catalyst components during the synthesis thereof.

The loading (during the synthesis) molar ratio of internal donor (ID) to the compound of a metal of Group 1 to 3 (iii), in particular Mg, (ID/Mg), is preferably from 0.010 to 0.300 mol/mol and more preferably from 0.030 to 0.250 mol/mol and even more preferably from 0.040 to 0.120 mol/mol.

Other Compounds of the Ziegler-Natta Catalyst Component

In addition to the internal donor (i), the Ziegler-Natta catalyst component of the present invention further comprises
(ii) a compound of a transition metal of Group 4 to 6 of the Periodic Table (IUPAC, Nomenclature of Inorganic Chemistry, 2005);
(iii) a compound of a metal of Group 1 to 3 of the Periodic Table (IUPAC, 2005); and
(iv) optionally, a compound of Group 13 element of the Periodic Table (IUPAC, 2005).

The Ziegler-Natta catalyst component is typically solid. The solid Ziegler-Natta catalyst component may be formed without using any external support material or it can be a solid Ziegler-Natta catalyst component based on an external support material.

The solid supported Ziegler-Natta catalyst component comprises
(i) an internal donor selected from compounds of formula (I) as discussed herein;
(ii) compound of a transition metal of Group 4 to 6 of the Periodic Table (IUPAC, Nomenclature of Inorganic Chemistry, 2005), in particular a titanium compound;
(iii) a compound of a metal of Group 1 to 3 of the Periodic Table (IUPAC, 2005), in particular a magnesium compound; and
(iv) optionally, a compound of Group 13 element of the Periodic Table (IUPAC, 2005), in particular an aluminium compound;
wherein components (i) to (iv), when present, are supported on a solid support.

The solid support can be selected from a group consisting of an inorganic oxide solid support, such as silica, alumina, titania, silica-alumina, silica-titania and a Mg-based solid support, such as a $MgCl_2$ based solid support. Preferably, the solid support is silica or a Mg-based solid support, such as a $MgCl_2$-based solid support, more preferably the solid support is solid support of particles of the $MgCl_2*mROH$ adduct, wherein R in the adduct $MgCl_2*mROH$ is a linear or branched $C_{1-12}$-alkyl group, and m is 0 to 6, preferably 1 to 6. More preferably, m is 1 to 4.

The volume-based median particle size ($D_{v0.5}$) of a silica support is typically from 2 to 500 μm, preferably 5 to 200 μm, more preferably 10 to 100 μm. However, it has turned out, that special advantages can be obtained if the support has $D_{v0.5}$ particle size from 5 to 30 μm, preferably from 7 to 20 μm, more preferably from 8 to 15 μm. Alternatively, the silica support may have a $D_{v0.5}$ particle size preferably from 20 to 80 μm, more preferably from 20 to 30 μm. Examples of suitable silica support materials comprise, for instance, ES747JR produced and marketed by Ineos Silicas (former Crossfield) and SP9-491, produced and marketed by Grace.

The catalyst component can be prepared by sequentially contacting the carrier with the above mentioned compounds, as described e.g. in EP0688794 A1 and WO99/51646 A1. Alternatively, it can be prepared by first preparing a solution from the components and then contacting the solution with a carrier, as described in WO01/55230 A1.

Alternatively, the catalyst component used in the present invention may be supported on a Mg-based solid support, in particular $MgCl_2$. Thus, the catalyst comprises a titanium compound and optionally a compound of a Group 13 element, for example an aluminium compound, on a magnesium dihalide, such as magnesium dichloride. A group of such Ziegler-Natta catalyst components comprises a titanium compound together with a magnesium halide compound acting as a support. Such catalysts are disclosed, for instance, in WO2005/118655 A1, EP0810235 A2, WO2014/096296 A1 and WO2016/097193 A1.

The catalyst component may, for example, be prepared by contacting spheroidal or granular $MgCl_2 \cdot mROH$, such as $MgCl_2 \cdot mEtOH$, carrier material with an internal electron donor selected from compounds of formula (I) in the beginning of the catalyst synthesis, i.e. prior to a treatment with the titanium compound (e.g. $TiCl_4$) or even prior to a treatment of the $MgCl_2 \cdot mEtOH$ carrier material with a compound of a Group 13 element, and by finally recovering the solid catalyst component.

The median particle size $D_{v0.5}$ of a Mg-based solid support is typically from 2 to 500 µm, preferably 5 to 200 µm, more preferably 10 to 100 µm. However, it has turned out that special advantages can be obtained if the support has a $D_{v0.5}$ particle size from 5 to 30 µm, preferably from 7 to 25 µm, more preferably from 8 to 20 µm, or even from 8 to 15 µm. Alternatively, the support may have a $D_{v0.5}$ particle size of from 20 to 80 µm, preferably from 20 to 30 µm. $MgCl_2 \cdot mROH$ can be prepared by methods described in prior art. Preparation methods of $MgCl_2 \cdot mROH$ carrier are described in several patents e.g. in EP0376936 B1, EP0424049 B1, EP0655073 B1, U.S. Pat. No. 4,071,674 and EP0614467 B1, which are incorporated herein by reference.

Solid Ziegler-Natta catalyst components may be alternatively formed without using any external support material, such as silica, alumina or separately prepared Mg-based solid support, onto which active catalyst components are loaded. Instead, a solid catalyst is formed by a method, where all active catalyst compounds are contacted and/or reacted in liquid form with each other and, after that, the solid catalyst component is formed.

In an embodiment of the present invention, the Ziegler-Natta catalyst component comprises
  (i) an internal donor selected from compounds of formula (I) as discussed herein;
  (ii) a Group 4 to 6 metal, preferably a Group 4 metal, more preferably Ti, content (determined by ICP Analysis) in the range of 1.0 wt % to 15.0 wt %, preferably 2.5 wt % to 12.0 wt %, more preferably 3.0 wt % to 10.0 wt % of the total weight of the Ziegler-Natta catalyst component;
  (iii) a Group 1 to 3, preferably a Group 2 metal, more preferably Mg, content (determined by ICP Analysis) in the range of 5.0 wt % to 30.0 wt %, preferably 9.0 wt % to 22.0 wt %, more preferably 13.0 wt % to 21.0 wt % of the total weight of the Ziegler-Natta catalyst component;
  (iv) an Al content (determined by ICP Analysis) in the range of 0.0 wt % to 3.0 wt %, preferably 0.0 wt % to 2.6 wt %, more preferably 0.0 wt % to 1.5 wt % of the total weight of the Ziegler-Natta catalyst component.

Further, the Ziegler-Natta catalyst component according to the embodiment of the present invention has a volume-based median particle size $(D_{v0.5})$ in the range of 2 to 100 µm, preferably 5 to 30 µm, more preferably 8 to 25 µm, even more preferably 8 to 20 µm, particularly 8 to 15 µm.

Transition Metal Compound of Group 4 to 6 (ii)

The compound of a transition metal of Group 4 to 6 of the Periodic Table (IUPAC, Nomenclature of Inorganic Chemistry, 2005), is preferably a compound of a transition metal of Group 4 of the Periodic Table (IUPAC, 2005), or a vanadium compound, more preferably a titanium or vanadium compound, even more preferably a titanium compound, yet even more preferably a halogen containing titanium compound, most preferably a chlorine containing titanium compound.

Particularly preferably the titanium compound is a halogen-containing titanium compound of the formula $Hal_yTi(OAlk)_{4-y}$, wherein Alk is a $C_{1-20}$-alkyl group, preferably a $C_{2-10}$-alkyl group, and more preferably a $C_{2-8}$-alkyl group, Hal is halogen, preferably chlorine and y is 1, 2, 3 or 4, preferably 3 or 4 and more preferably 4.

Suitable titanium compounds include trialkoxytitanium monochlorides, dialkoxytitanium dichlorides, alkoxytitanium trichlorides, and titanium tetrachloride. Preferably, titanium tetrachloride is used.

The amount of the compound of Group 4 to 6 in the Ziegler-Natta catalyst component is preferably such that the content of the Group 4 to 6 metal, preferably Group 4 metal, more preferably Ti (determined by ICP Analysis) is in the range of 1.0 wt % to 15.0 wt %, preferably 2.5 wt % to 12.0 wt %, more preferably 3.0 wt % to 10.0 wt % of the total weight of the Ziegler-Natta catalyst component. The amount of the compound of Group 4 to 6 metal is determined by ICP Analysis as described in the Experimental part.

Metal Compound of Group 1 to 3 (iii)

The metal compound of Group 1 to 3 is preferably a metal compound of Group 2 of the Periodic Table (IUPAC, Nomenclature of Inorganic Chemistry, 2005), more preferably a magnesium compound.

The amount of the compound of Group 1 to 3 metal in the Ziegler-Natta catalyst component is preferably such that a Group 1 to 3 metal, preferably a Group 2 metal, more preferably Mg, content is in the range of 5.0 wt % to 30.0 wt %, preferably 9.0 wt % to 22.0 wt %, more preferably 13.0 wt % to 21.0 wt % of the total weight of the Ziegler-Natta catalyst component. The amount of the metal compound of Group 1 to 3 is determined by ICP Analysis as described in the Experimental part.

In a particular example the metal compound of Group 1 to 3 is provided in the form of a $MgCl_2$-based solid support, preferably solid support particles of $MgCl_2 \cdot mROH$ adduct, wherein R in the adduct $MgCl_2 \cdot mROH$ is a linear or branched $C_{1-12}$-alkyl group, and m is 0 to 6, preferably 1 to 6, more preferably 1 to 4.

Preferably, the final solid Ziegler-Natta catalyst component particles have a median particle size $D_{0.5}$ in the range of 2 to 100 µm, preferably 5 to 30 µm, more preferably 8 to 20 µm, even more preferably 8 to 15 µm.

Compound of Group 13 Element (iv)

The optional compound of the Group 13 element of the Periodic Table (IUPAC, Nomenclature of Inorganic Chemistry, 2005) is preferably an aluminium compound.

Particularly preferably the aluminium compound is an aluminium compound of the formula $Al(alkyl)_xHal_{3-x}$(II), wherein each alkyl is independently an $C_{1-12}$-alkyl group, preferably $C_{1-8}$-alkyl group, more preferably $C_{1-6}$-alkyl group, Hal is halogen, preferably chlorine and $1 < x \leq 3$. The alkyl group can be linear, branched or cyclic, or a mixture of such groups.

Preferred aluminium compounds are alkylaluminium dichlorides, dialkylaluminium chlorides or trialkylaluminium compounds, for example dimethylaluminium chloride, diethylaluminium chloride, di-isobutylaluminium chloride, and triethylaluminium or mixtures thereof. Most preferably, the aluminium compound is a trialkylaluminium compound, especially triethylaluminium.

The amount of the compound of the Group 13 element in the Ziegler-Natta catalyst component is preferably such that the Group 13 element, preferably Al, content is in the range of 0.0 wt % to 3.0 wt %, preferably 0.0 wt % to 2.6 wt %, more preferably 0.0 wt % to 1.5 wt % of the total weight of the Ziegler-Natta catalyst component. The amount of the Group 13 element is determined by ICP Analysis as described in the Experimental part.

The internal donor is a part of the Ziegler-Natta catalyst component and is added to said Ziegler-Natta catalyst component during the synthesis thereof.

The molar loading ratio (in the synthesis) of internal donor (ID) to the metal of Group 1 to 3 (iii), in particular Mg (ID/Mg), is preferably from 0.010 to 0.300 mol/mol and more preferably from 0.030 to 0.250 mol/mol and even more preferably from 0.040 to 0.120 mol/mol.

The final Ziegler-Natta catalyst component typically has:
a Mg/Ti mol/mol ratio of 2.0 to 15.0, preferably 2.5 to 12.0, more preferably 3.0 to 10.0;
an Al/Ti mol/mol ratio 0 to 1.0, preferably 0 to 0.8, more preferably 0 to 0.5; and
a Cl/Ti mol/mol ratio of 5.0 to 30.0, preferably 6.0 to 27.0, more preferably 8.0 to 23.0.

Method for Producing the Ziegler-Natta Catalyst Component

Generally, the present Ziegler-Natta catalyst component as defined herein is produced by adding the present internal donor, i.e. compound of formula (I), to a process of preparing the Ziegler-Natta catalyst component. This may be accomplished by manners and under conditions that are well known to the person skilled in the art of making Ziegler-Natta catalysts.

Accordingly, provided herein is a method for producing a Ziegler-Natta catalyst component, in particular a Ziegler-Natta catalyst component as defined herein, comprising a step of adding an internal donor of formula (I) as defined herein to a process of preparing the Ziegler-Natta catalyst component.

A solid Ziegler-Natta catalyst component can, for example, be prepared by sequentially contacting a solid support, such as silica, alumina or separately prepared Mg-based solid support, such as $MgCl_2$-based solid support, with the above-mentioned compounds, as described in EP0376936 A1, EP0688794 A1 or WO99/51646 A1. Alternatively, it can be prepared by first preparing a solution from the components and then contacting the solution with a solid support, as described in WO01/55230 A1.

In a particular example of the present method, the method for producing the Ziegler-Natta catalyst component comprises the steps of
(M-a) providing a solid support, preferably $MgCl_2$-based solid support, more preferably solid support particles of $MgCl_2*mROH$ adduct, wherein R in the $MgCl_2*mROH$ adduct is a linear or branched $C_{1-12}$-alkyl group, and m is 0 to 6, preferably 1 to 6, more preferably 1 to 4;
(M-b) pre-treating the solid support particles of step (M-a) with a compound of a Group 13 element;
(M-c) treating the pre-treated solid support particles of step (M-b) with a transition metal compound of Group 4 to 6;
(M-d) recovering the Ziegler-Natta catalyst component;
wherein the solid support is contacted with an internal electron donor of formula (I) or mixtures therefrom before treating the solid support in step (M-c).

Preferably, the compound of formula (I), as defined herein, is added to the catalyst mixture before, during or after the pre-treating of the solid support with the compound of Group 13 element, but before treating it with the compound of a transition metal of Group 4 to 6.

Solid Ziegler-Natta catalyst components may also be formed without using any external support material, like silica, alumina or separately prepared Mg-based solid support, onto which active catalyst components are loaded. In this case, a solid catalyst is formed by a method where all active catalyst compounds are contacted and/or reacted in liquid form with each other, and after that the solid catalyst is formed. The solid Ziegler-Natta catalyst components may be formed via emulsion-solidification or via precipitation method. Whether a Ziegler-Natta catalyst component is formed via emulsion-solidification or via precipitation method depends on the conditions, especially on the temperature used during contacting the compounds. In the emulsion-solidification method the compounds of the Ziegler-Natta catalyst component form a dispersed, i.e. a discontinuous phase in the emulsion of at least two liquid phases. The dispersed phase, in the form of droplets, is solidified from the emulsion, wherein the Ziegler-Natta catalyst component in the form of solid particles is formed. The principles of preparation of these types of catalysts are given e.g. in WO2003/106510 A1, WO2013/098139 A1 and WO2014/096297 A1.

Zieqler-Natta Catalyst

Accordingly further provided herein is a Ziegler-Natta catalyst for olefin polymerization, in particular for ethylene (co)polymerization, comprising a Ziegler-Natta catalyst component comprising an internal electron donor selected from compounds of formula (I)

(I)

wherein
$X_1$ and $X_2$ are each independently selected from O and $N(R_5)$;
$R_1$ is selected from a group consisting of H, $C_{1-3}$-alkyl, and oxygen-containing heterocyclic ring; and
$R_2$ is selected from H and methyl, with the provisio that only one of $R_1$ and $R_2$ may be H;
$R_3$ and $R_4$ are independently selected from $C_{1-2}$-alkyl; and
$R_5$ is selected from a group consisting of H, a linear, branched or cyclic $C_{1-8}$-alkyl group.

Preferably, $R_1$ is selected from a group consisting of H, methyl, tetrahydrofuryl and furyl. More preferably, $R_1$ is selected from a group consisting of H, methyl, 2-tetrahydrofuryl and 2-furyl.

Preferably $R_3$ and $R_4$ are independently selected from $C_{1-2}$-alkyl, more preferably $R_3$ and $R_4$ are methyl.

Preferably, $R_5$ is selected from a group consisting of H, a linear or branched $C_{1-4}$-alkyl group, more preferably $R_5$ is methyl.

In a first example of the Ziegler-Natta catalyst, the compound of formula (I) is selected from compounds of formula (I-a)

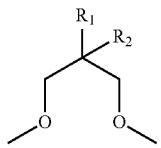

(I-a)

wherein
$R_1$ is selected from a group consisting of H, $C_{1-3}$-alkyl, and oxygen-containing heterocyclic ring; and
$R_2$ is selected from H and methyl, with the proviso that only one of $R_1$ and $R_2$ may be H.

Preferably, $R_1$ is selected from a group consisting of H, methyl, tetrahydrofuryl and furyl. More preferably, $R_1$ is selected from a group consisting of H, methyl, 2-tetrahydrofuryl and 2-furyl.

In a second example of the Ziegler-Natta catalyst, the compound of formula (I) is selected from compounds of formula (I-b)

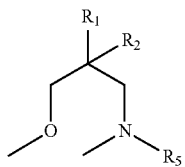

(I-b)

wherein
$R_1$ is selected from a group consisting of H, $C_{1-3}$-alkyl, and oxygen-containing heterocyclic ring;
$R_2$ is selected from H and methyl; and
$R_5$ is selected from a group consisting of H, a linear or branched or cyclic $C_{1-8}$-alkyl group.

Preferably, $R_1$ is selected from a group consisting of H, methyl, tetrahydrofuryl and furyl. More preferably, $R_1$ is selected from a group consisting of H, methyl, 2-tetrahydrofuryl and 2-furyl. Even more preferably, $R_1$ is H.

Preferably, $R_5$ is selected from a group consisting of H, a linear, branched $C_{1-3}$-alkyl group, more preferably methyl.

In a particular example the compound of formula (I) is selected from a group consisting of 1,3-dimethoxy-2-methylpropane, 2,2-dimethyl-1,3-dimethoxypropane, 2-(1,3-dimethoxypropan-2-yl)tetrahydrofuran, 2-(1,3-dimethoxypropan-2-yl)furan, 2-(1,3-dimethoxy-2-methylpropan-2-yl)tetrahydrofuran, 2-(1,3-dimethoxy-2-methylpropan-2-yl)furan, and 3-methoxy-N,N-dimethylpropan-1-amine. In a further particular example the compound of formula (I) is selected from a group consisting of 1,3-dimethoxy-2-methylpropane, 2,2-dimethyl-1,3-dimethoxypropane, 2-(1,3-dimethoxypropan-2-yl)tetrahydrofuran, 2-(1,3-dimethoxypropan-2-yl)furan, 2-(1,3-dimethoxy-2-methylpropan-2-yl)tetrahydrofuran, and 2-(1,3-dimethoxy-2-methylpropan-2-yl)furan.

In particular, the present Ziegler-Natta catalyst comprises
(A) a Ziegler-Natta catalyst component as defined herein;
(B) a cocatalyst selected from compounds of Group 13 element of the Periodic Table (IUPAC, 2005); and
(C) optionally an external donor.

(B) Cocatalyst (II)

A Ziegler-Natta catalyst is typically used together with a cocatalyst, also known as activator. Suitable cocatalysts are compounds of elements of Group 13 of the Periodic Table (IUPAC, 2005), typically Group 13 element $C_{1-16}$-alkyl compounds and especially aluminium $C_{1-16}$-alkyl compounds. These compounds include trialkylaluminium compounds, such as trimethylaluminium, triethylaluminium, tri-isobutylaluminium, trihexylaluminium and tri-n-octylaluminium, alkyl aluminium halides, such as ethylaluminium dichloride, diethylaluminium chloride, ethylaluminium sesquichloride, dimethylaluminium chloride and the like. Especially preferred activators are trialkylaluminiums, of which triethylaluminium, trimethylaluminium and tri-isobutylaluminium are particularly used.

The amount in which the cocatalyst is used depends on the specific catalyst and the cocatalyst. Typically, e.g. triethylaluminium is used in such amount that the molar ratio of aluminium to the transition metal, such as Al/Ti, is from 1 to 1000, preferably from 3 to 100 and in particular from about 5 to about 30 mol/mol.

(C) External Donor

The catalyst of the invention may also comprise an external donor. External donors that can be used include ether compounds, typically tetrahydrofuran, siloxane or silane type external donors and/or alkyl halides as are known from the prior art. External donors are also called external electron donors. External electron donors are not part of the solid catalyst component, but are fed to the polymerization process as a separate component.

Polymerization of Olefins

The present Ziegler-Natta catalyst components as defined herein, in particular Ziegler-Natta catalysts as defined herein, are intended for polymerizing olefins, preferably ethylene, optionally with $C_{2-20}$ comonomers.

Accordingly provided herein is the use of Ziegler-Natta catalyst component as defined herein or a Ziegler-Natta catalyst as defined herein in olefin polymerization, preferably ethylene polymerization, optionally with $C_{2-20}$ comonomers.

Furthermore, provided herein is a method of olefin polymerization, in particular of ethylene (co)polymerization, which comprises introducing into a polymerization reactor a Ziegler-Natta catalyst comprising a Ziegler-Natta catalyst component, the Ziegler-Natta catalyst component comprising an internal donor of formula (I) as defined herein.

Preferably, a Ziegler-Natta catalyst component as defined herein or a Ziegler-Natta catalyst as defined herein is used in ethylene polymerization, optionally with one or more comonomers. Commonly used comonomers in ethylene polymerization are α-olefin comonomers. The α-olefin comonomers are preferably selected from $C_{3-20}$-α-olefins, more preferably from $C_{4-10}$-α-olefins, such as 1-butene, isobutene, 1-pentene, 1-hexene, 4-methyl-1-pentene, 1-heptene, 1-octene, 1-nonene and 1-decene, as well as dienes, such as butadiene, 1,7-octadiene and 1,4-hexadiene, or cyclic olefins, such as norbornene, and any mixtures thereof. Most preferably, the comonomer is 1-butene and/or 1-hexene.

The catalyst of the present invention allows for the production of a wide range of polyethylene (co)polymers. Thus, production of high density, medium density and low-density ethylene (co)polymers is possible.

If copolymers are the desired end-product, the comonomer content of the ethylene copolymers can vary in wide ranges depending on the desired polymer properties. Thus, the comonomer content can vary from 0.1 wt % to 20 wt %, preferably 0.5 wt % to 15 wt % and more preferably from 1.0 wt % to 10 wt %.

Further provided herein is a process for producing ethylene homo- or copolymers, comprising the steps of
- (P-a) introducing a Ziegler-Natta catalyst component as defined herein into a polymerization reactor,
- (P-b) introducing a cocatalyst capable of activating said Ziegler-Natta catalyst component into the polymerization reactor,
- (P-c) introducing ethylene, optionally $C_3$-$C_{20}$ α-olefin comonomers, and optionally hydrogen into the polymerization reactor; and
- (P-d) maintaining said polymerization reactor in such conditions as to produce an ethylene homo- or copolymer.

The catalyst may be transferred into the polymerization zone by any means known in the art. It is thus possible to suspend the catalyst in a diluent and maintain it as homogeneous slurry. It is especially preferred to use an oil having a viscosity from 20 to 1500 mPa·s as diluent, as disclosed in WO2006/063771 A1. It is also possible to mix the catalyst with a viscous composition of grease and oil and feed the resultant paste into the polymerization zone. Further still, it is possible to let the catalyst settle and introduce portions of thus obtained catalyst mud into the polymerization zone in a manner disclosed, for instance, in EP0428054 A1.

The polymerization process used according to the present invention comprises at least one gas phase reactor, or at least one slurry reactor or a combination of at least one slurry and at least one gas phase reactor.

The polymerization in slurry usually takes place in an inert diluent, typically a hydrocarbon diluent such as methane, ethane, propane, n-butane, isobutane, pentanes, hexanes, heptanes, octanes etc., or their mixtures. Preferably, the diluent is a low-boiling hydrocarbon having from 1 to 4 carbon atoms or a mixture of such hydrocarbons. An especially preferred diluent is propane, possibly containing minor amount of methane, ethane and/or butane.

The temperature in the slurry polymerization is typically from 40 to 115° C., preferably from 60 to 110° C. and in particular from 70 to 100° C. The pressure is from 1 to 150 bar, preferably from 10 to 100 bar.

The slurry polymerization may be carried out in any known reactor used for slurry polymerization. Such reactors include a continuous stirred tank reactor and a loop reactor.

It is especially preferred to conduct the polymerization in loop reactor. Hydrogen is fed, optionally, into the reactor to control the molecular weight of the polymer as known in the art.

Furthermore, one or more alpha-olefin comonomers may be added to the reactor to control the density and morphology of the polymer product. The actual amount of such hydrogen and comonomer feeds depends on the desired melt index (or molecular weight) and density (or comonomer content) of the resulting polymer.

The polymerization in gas phase may be carried out in a fluidized bed reactor, in a fast-fluidized bed reactor or in a settled bed reactor or in any combination of these.

Typically, the fluidized bed or settled bed polymerization reactor is operated at a temperature within the range of from 50 to 100° C., preferably from 65 to 90° C. The pressure is suitably from 10 to 40 bar, preferably from 15 to 30 bar.

In addition, antistatic agent(s) may be introduced into the slurry and/or gas phase reactor if needed.

The process may further comprise pre- and post-reactors.

The polymerization steps may be preceded by a pre-polymerization step. The pre-polymerization step may be carried out in slurry or in gas phase. Preferably, pre-polymerization is carried out in slurry, and especially in a loop reactor. The temperature in the pre-polymerization step is typically from 0 to 90° C., preferably from 20 to 80° C. and more preferably from 30 to 70° C.

The pressure is not critical and is typically from 1 to 150 bar, preferably from 10 to 100 bar.

The polymerization may be carried out continuously or batch-wise, preferably the polymerization is carried out continuously.

A preferred multi-stage process for producing ethylene (co)polymers according to the invention comprises a slurry phase polymerization stage and a gas phase polymerization stage. Each stage can comprise one or more polymerization reactors. One suitable reactor configuration comprises one to two slurry reactors, preferably loop reactors and one gas phase reactor. Such polymerization configuration is described e.g. in patent literature, such as in WO92/12182 A1 and WO96/18662 A1 of *Borealis* and known as Borstar technology.

In a first example of the present process, polymerizing olefins is accomplished in a multi-stage polymerization process comprising at least one gas phase reactor for producing ethylene (co)polymers.

In a second example of the present process, polymerizing olefins is accomplished in a multi-stage polymerization process comprising at least one slurry reactor, preferably two slurry reactors, and one gas phase reactor.

Polymer Properties

By utilizing the present internal donor in a Ziegler-Natta catalyst component in a polymerization process according to the present invention it is possible to produce ethylene (co)polymers having desirable molecular weight, molecular weight distribution (MWD) and chemical composition distribution (CCD) while keeping the productivity on a good level as shown by the below examples.

The molecular weight, molecular weight distribution (MWD) and chemical composition distribution (CCD) of the produced polymer can be optimized by utilization of the present internal donors in Ziegler-Natta catalysts.

Further, the improvements, like the increase in molecular weight and/or the narrowing of MWD, are not obtained at the expense of the productivity of the catalyst, but the productivity remains at an acceptably high level. Thus, the performance of Ziegler-Natta catalysts comprising the present internal donors renders the improvements, such as the increase in molecular weight and/or the narrowing of MWD, which are not obtained at the expense of the productivity of the catalyst, but the productivity remains at an acceptably high level.

Especially an optimal combination of hydrogen response, MWD, comonomer response, chemical composition distribution (CCD), catalyst activity and productivity makes the utilization of the present internal donors in Ziegler-Natta catalysts very attractive for producing polyethylene (co)polymers.

The advantages of the present invention are shown in the experimental part and in the figures:

FIG. 1: In FIG. 1 polydispersity index (PDI) vs. molecular weight of polymers of inventive examples (IE1-IE8) and comparative examples CE1 and CE2 is disclosed.

Figure 2:
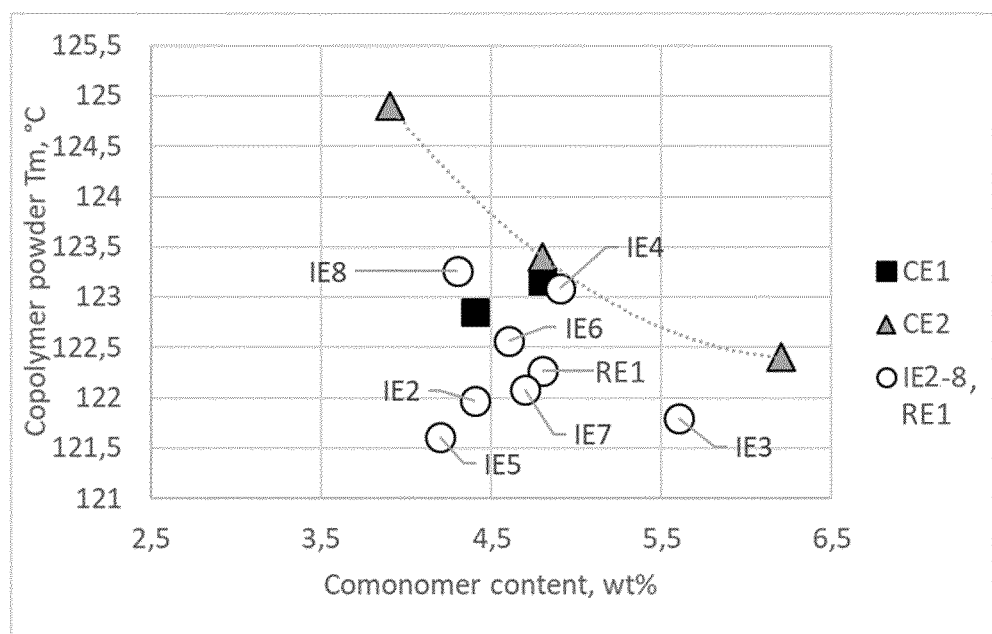

FIG. 2: In FIG. 2 melting temperature vs. comonomer content of polymers of inventive examples (IE1-IE8) and comparative examples CE1 and CE2 is disclosed.

Figure 3:
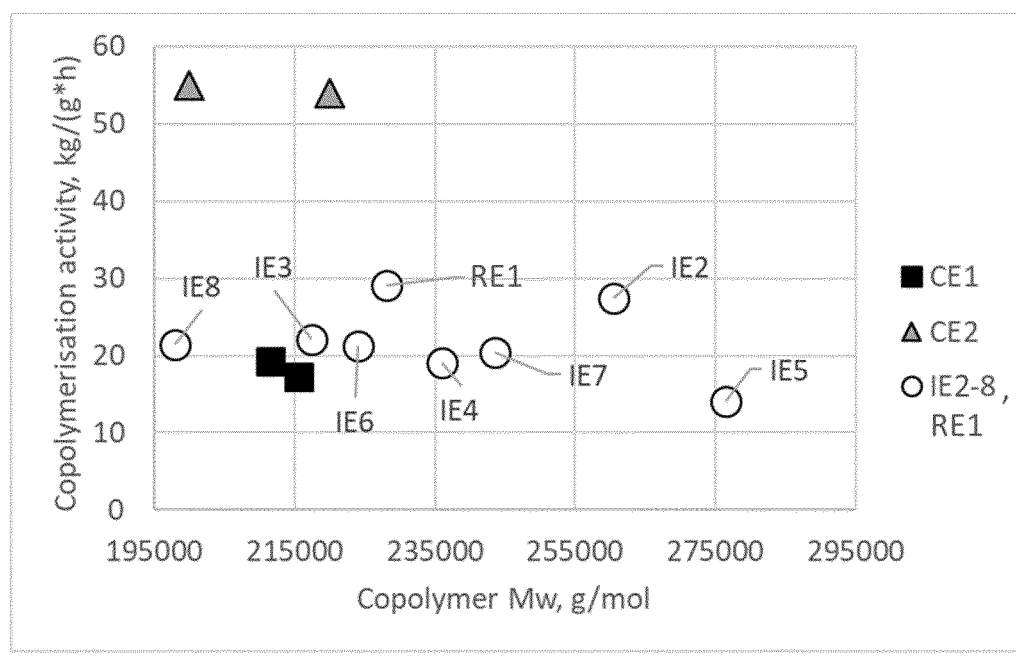

FIG. 3: In FIG. 3 activity vs. molecular weight of polymers of inventive examples (IE1-IE8) and comparative examples CE1 and CE2 is disclosed.

EXPERIMENTAL PART

Analytical Methods
Al, Mq, Ti Contents in a Catalyst Component by ICP-OES

The sample consisting of dry catalyst component powder is mixed so that a representative test portion can be taken. Approximately 20-50 mg of material is sampled in inert atmosphere into a 20 mL volume vial and the exact weight of powder recorded.

A test solution of known volume (V) is prepared in a volumetric flask as follows. Sample digestion is performed in the cooled vial by adding a small amount of deionized and distilled (DI) water (5% of V), followed by adding concentrated nitric acid (65% $HNO_3$, 5% of V). The mixture is transferred into a volumetric flask. The solution diluted with DI water up to the final volume V, and left to stabilise for two hours.

The elemental analysis of the resulting aqueous samples is performed at room temperature using a Thermo Elemental iCAP 6300 Inductively Coupled Plasma-Optical Emission Spectrometer (ICP-OES). The instrument is calibrated for Al, Ti and Mg using a blank (a solution of 5% $HNO_3$) and six standards of 0.5 ppm, 1 ppm, 10 ppm, 50 ppm, 100 ppm and 300 ppm of Al, Ti and Mg in solutions of 5% $HNO_3$ DI water. Curvelinear fitting and 1/concentration weighting is used for the calibration curve.

Immediately before analysis the calibration is verified and adjusted (instrument function named "re-slope") using the blank and a 300 ppm Al, 100 ppm Ti, Mg standard. A quality control sample (QC; 20 ppm Al and Ti, 50 ppm Mg in a solution of 5% $HNO_3$ in DI water) is run to confirm the re-slope. The QC sample is also run after every $5^{th}$ sample and at the end of a scheduled analysis set.

The content of magnesium is monitored using the 285.213 nm line and the content for titanium using 336.121 nm line. The content of aluminium is monitored via the 167.079 nm line, when Al concentration in test portion is between 0-10 wt % and via the 396.152 nm line for Al concentrations above 10 wt %.

The reported values are an average of results of three successive aliquots taken from the same sample and are related back to the original catalyst sample based on input into the software of the original weight of test portion and the dilution volume.

Cl Content in a Catalyst Component by Potentiometric Titration

Chloride content of catalyst components is determined by titration with silver nitrate. A test portion of 50-200 mg of a catalyst component is weighed under nitrogen in a septum-sealed vial. A solution of 1 part of concentrated $HNO_3$ (68%, analytical grade) and 4 parts of deionized and distilled (DI) water are added to the sample in an aliquot of 2.5 mL using a syringe. After the reaction completion and dissolution of the catalyst component material, the solution is transferred into a titration cup using an excess of DI water. The solution is then immediately titrated with a commercially certified solution of 0.1 M $AgNO_3$ in a Mettler Toledo T70 automatic titrator. The titration end-point is determined using an Ag-electrode. The total chloride amount is calculated from the titration and related to the original sample weight.

Volatiles in a Catalyst Component by GC-MS

A test solution using a 40-60 mg test portion of catalyst component powder is prepared by liquid-liquid extraction of the sample and internal standard in water and dichloromethane: first, 10 mL of dichloromethane are added to the test portion, followed by addition of 1 mL of the internal standard solution (dimethyl pimelate, 0.71 vol % in deionized water) using a precision micro-syringe. The suspension is sonicated for 30 min and left undisturbed for phase separation. A portion of the test solution is taken from the organic phase and filtered using a 0.45 μm syringe filter.

For the calibration, five standard stock solutions with different analyte concentrations are prepared by dosing five increasing portions of analyte standard materials accurately into volumetric flasks and filling up to mark with methanol. For the preparation of the calibration samples, aliquots of 200 μL from the stock solutions are extracted with the aqueous ISTD solution and dichloromethane in the same volume ratios as for the samples. The analyte amount in the final calibration samples ranges from 0.1 mg to 15 mg.

The measurement is performed using an Agilent 7890B Gas Chromatograph equipped with an Agilent 5977A Mass Spectrometer Detector. The separation is achieved using a ZB-XLB-HT Inferno 60 m×250 μm×0.25 μm column (Phenomenex) with midpoint backflush through a three channel auxiliary EPC and a pre-column restriction capillary of 3 m×250 μm×0 μm. The initial oven temperature is 50° C. and the hold time is 2 min. The oven ramp consists of a first stage of 5° C./min to 150° C. and a second stage of 30° C./min to 300° C. followed by a 1 min post-run backflush at 300° C.

The inlet operates in split mode. Injection volume is 1 μL, inlet temperature 280° C., septa purge 3 mL/min, total flow 67.875 mL/min and split ratio 50:1. Carrier gas is 99.9996% He with pre-column flow of 1.2721 mL/min and additional flow of 2 mL/min from the backflush EPC to the analytical column. The MS detector transfer line is kept at 300° C. The MSD is operated in Electron Impact mode at 70 eV and Scan mode ranging from 15-300 m/z.

The signal identities are determined by retention times (heptane 4.8, toluene 6.3, dimethyl-pimelate 23.2) and target ion m/z (heptane 71.1, toluene 91.1, dimethyl pimelate 157.1). Additionally, qualifier ions are used for confirmation of the identification (heptane, toluene). The target ion signals of each analyte and the internal standard are integrated and compared to calibration curve, established in the beginning of each run with the five calibration samples. The calibration curves for the response ratios are linear without sample concentration weighting. A quality control sample is used in each run to verify the standardization. All test solutions are run in two replicate runs. The mass of the test portion is used for calculating the analyte concentration in the sample for both replicates and the result reported as the average.

Polymer Melting and Crystallization Properties by DSC

Polymer Differential Scanning calorimetry analysis (DSC) is performed using a Mettler Toledo DSC2 on 5-10 mg samples. The polymer powder or pellet cut or MFR string cut sample is placed in a 40 μL aluminium pan, weighed to the nearest 0.01 mg and the pan is sealed with a lid. DSC is run according to ISO 11357-3 or ASTM D3418 in a heat/cool/heat run cycle with a scan rate of 10° C./min. The flow of nitrogen purge gas is set to 50-80 mL/min. The temperature range of the first heating run is 30° C. to 180° C. The temperature range of the cooling run and the second heating run is 180° C. to 0° C. (or lower). The isotherm times for the first heating run and the cooling run are 5 min. The first melting run is used to remove the thermal history of the sample. Crystallization temperature ($T_c$) is determined from the cooling run, while main melting temperature ($T_m$), degree of crystallinity (Cryst. %) and heat of melting ($H_m$) are determined from the second heating run.

Polymer Melt Flow Rate

The melt flow rates are measured in accordance with ISO 1133 at 190° C. and under given load and is indicated in units of grams/10 minutes. The melt flow rate is an indication of the molecular weight of the polymer. The higher the melt flow rate, the lower the molecular weight of the polymer.

$MFR_{21}$: 190° C., 21.6 kg load

Molecular Weight Averages, Molecular Weight Distribution ($M_n$, $M_w$, $M_z$, MWD, PDI)

Molecular weight averages ($M_z$, $M_w$ and $M_n$), Molecular weight distribution (MWD) and its broadness, described by polydispersity index, $PDI = M_w/M_n$ (wherein $M_n$ is the number average molecular weight and $M_w$ is the weight average molecular weight) were determined by Gel Permeation Chromatography (GPC) according to ISO 16014-1:2003, ISO 16014-2:2003, ISO 16014-4:2003 and ASTM D 6474-12 using the following formulas:

$$M_n = \frac{\sum_{i=1}^{N} A_i}{\sum_{i=1}^{N} (A_i/M_i)} \quad (1)$$

$$M_w = \frac{\sum_{i=1}^{N} (A_i \times M_i)}{\sum_{i=1}^{N} A_i} \quad (2)$$

$$M_Z = \frac{\sum_{i=1}^{N} (A_i \times M_i^2)}{\sum_{i=1}^{N} (A_i/M_i)} \quad (3)$$

For a constant elution volume interval $\Delta V_i$, where $A_i$, and $M_i$, are the chromatographic peak slice area and polyolefin molecular weight (MW), respectively associated with the elution volume, $V_i$, where N is equal to the number of data points obtained from the chromatogram between the integration limits.

A high temperature GPC instrument, equipped with either infrared (IR) detector (IR4 or IR5 from PolymerChar (Valencia, Spain) or differential refractometer (RI) from Agilent Technologies, equipped with 3× Agilent-PLgel Olexis and 1× Agilent-PLgel Olexis Guard columns was used. As the solvent and mobile phase 1,2,4-trichlorobenzene (TCB) stabilized with 250 mg/L 2,6-Di tert butyl-4-methyl-phenol) was used. The chromatographic system was operated at 160° C. and at a constant flow rate of 1 mL/min. 200 µL of sample solution was injected per analysis. Data collection was performed using either Agilent Cirrus software version 3.3 or PolymerChar GPC-IR control software.

The column set was calibrated using universal calibration (according to ISO 16014-2:2003) with 19 narrow MWD polystyrene (PS) standards in the range of 0.5 kg/mol to 11500 kg/mol. The PS standards were dissolved at room temperature over several hours. The conversion of the polystyrene peak molecular weight to polyolefin molecular weights is accomplished by using the Mark Houwink equation and the following Mark Houwink constants:

$K_{PS} = 19 \times 10^{-3}$ mL/g, $\eta_{PS} = 0.655$
$K_{PE} = 39 \times 10^{-3}$ mL/g, $\eta_{PE} = 0.725$
$K_{PP} = 19 \times 10^{-3}$ mL/g, $\eta_{PP} = 0.725$ A third order polynomial fit was used to fit the calibration data.

All samples were prepared in the concentration range of 0.5-1 mg/mL and dissolved at 160° C. for 2.5 hours for PP or 3 hours for PE under continuous gentle shaking.

Polymer Comonomer Content (1-Butene) by FTIR

Comonomer content is determined based on Fourier transform infrared spectroscopy (FTIR) using Bruker Tensor 37 spectrometer together with OPUS software.

Approximately 0.3 grams of sample is compression-moulded into films with thickness of 250 µm. Silicone paper is used on both sides of the film. The films are not touched by bare hands to avoid contamination. The films are pressed by using Fontijne Press model LabEcon 300. The moulding is carried out at 160° C. with 2 min pre-heating+2 min light press+1 min under full press. The cooling is done under full press power for 4 minutes.

The butene comonomer content is determined from the absorbance at the wave number of approximately 1378 cm$^{-1}$ and the reference peak is 2019 cm$^{-1}$. The analysis is performed using a resolution of 2 cm$^{-1}$, wave number span from 4000 to 400 cm$^{-1}$ and the number of sweeps of 128. At least two spectra are obtained from each film.

The comonomer content is determined from a spectrum from the wave number range of 1400 cm$^{-1}$ to 1330 cm$^{-1}$. The baseline is determined using the following method: within the set wavenumber range, the highest peak is located and then the minima to the left and to the right of this highest peak. The baseline connects these minima. The absorbance value at the highest peak is divided by the area of the reference peak.

The calibration plot for the method is produced for each comonomer type separately. The comonomer content of an unknown sample needs to be within the range of the comonomer contents of the calibration samples. The comonomer content in the calibration sample materials is pre-determined by NMR-spectrometry.

The comonomer content is calculated automatically by using calibration curve and the following formula:

$$W_E = C_1 \times A_0 + C_0$$

where
$W_E$ = result in wt %
$A_0$ = absorbance of the measured peak ($A_Q$) to the area of the reference peak ($A_R$);
$C_1$ = slope of the calibration curve;
$C_0$ = offset of the calibration curve.

The comonomer content is determined from both of the obtained spectra and the value is calculated as the average of these results.

EXAMPLES

Comparative Internal Donor

CD1: 9,9-Di(methoxymethyl)fluorene (DMMF)

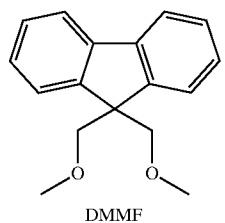

DMMF 9,9-Di(methoxymethyl)fluorene (CAS 182121-12-6), alternatively named 9,9-Bis(methoxymethyl)-9H-fluorene, was acquired from Hangzhou Sage Chemical Co.

Reference Internal Donors

RD1: 1,3-Dimethoxypropane (DMP)

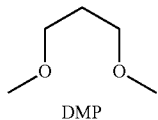
DMP 1,3-Dimethoxypropane (CAS 17081-21-9) was acquired from BOC Sciences.

Inventive Internal Donors

Inventive donors ID2 to ID7 were prepared according to the following procedures:

ID2: 1,3-Dimethoxy-2-methylpropane (DMMP)

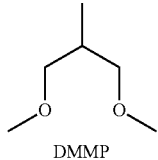
DMMP

To a suspension of 24.05 g (666.7 mmol, 2.5 eq.) of sodium hydride in 470 mL of THF a solution of 24.05 g (266.9 mmol) of 2-Methylpropane-1,3-diol and 95 g (669.3 mmol, 2.51 eq.) of methyl iodide in 200 mL of THF was added drop-wise for 2 h. After completion of the addition the reaction mixture was stirred overnight. Further on, the mixture was filtered through glass frit (G3), then 400 mL of water were added to the filtrate and the resulting mixture was extracted with 800 mL of n-hexane. The obtained organic extract was dried over sodium sulfate and distilled (b.p. 108-117° C.) under atmospheric pressure to give 20.36 g of 1,3-Dimethoxy-2-methylpropane contaminated with ~5 mol % of THF. This fraction was distilled once again to give 17.5 g (56%) of 1,3-Dimethoxy-2-methylpropane (CAS 210528-98-6) as a colorless liquid (b.p. 115° C.).

$^1$H NMR (CDCl$_3$, 400 MHz): δ 3.37-3.31 (s and dd, sum 8H), 3.24 (dd, J=9.3 Hz, J=6.2 Hz, 2H), 2.09-1.95 (m, 1H), 0.94 (d, J=6.9 Hz, 3H).

$^{13}$C{$^1$H} NMR (CDCl$_3$, 100 MHz): δ75.3, 58.9, 34.0, 14.3.

ID3: 1,3-Dimethoxy-2,2-dimethylpropane (DMDMP)

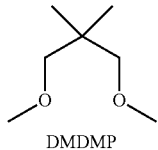
DMDMP

To a suspension of 16 g (666.7 mmol, 2.48 eq.) of sodium hydride in 470 mL of THF a solution of 28 g (268.9 mmol) of 2,2-Dimethylpropane-1,3-diol and 95 g (669.3 mmol, 2.49 eq.) of methyl iodide in 200 mL of THF was added drop-wise for 2 h. After completion of the addition the reaction mixture was stirred overnight. Further on, the reaction mixture was filtered through glass frit (G3), then 600 mL of water were added to the filtrate and the resulting mixture was extracted with 3×250 mL of n-hexane. The organic extracts were combined, dried over sodium sulfate, and rectified under atmospheric pressure to give 24.2 g (68%) of 1,3-Dimethoxy-2,2-dimethylpropane (CAS 20637-32-5) as a colorless liquid, b.p. 121-122° C.

$^1$H NMR (CDCl$_3$, 400 MHz): δ 3.33 (s, 6H), 3.14 (s, 4H), 0.89 (s, 6H).

$^{13}$C{$^1$H} NMR (CDCl$_3$, 100 MHz): δ79.1, 59.3, 36.1, 22.1.

ID4: 1,3-Dimethoxy-2-(2-tetrahydrofuryl)propane (DMTHFP)

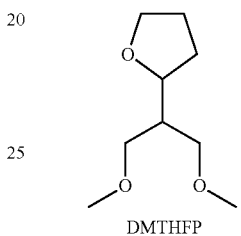
DMTHFP

Diethyl 2-(tetrahydrofuran-2-yl)malonate

A mixture of Diethyl (2-furyl)malonate (10.0 g, 44 mmol), 5% Pd/C (500 mg) and ethyl acetate (10 mL) was placed into a 200 mL autoclave which was purged with argon, pressurized with hydrogen (20 bar) and the mixture was stirred for 1 h at room temperature. After depressurization, the mixture was diluted with dichloromethane and filtered through a pad of Celite 503. The filtrate volatiles were evaporated in vacuum. The procedure afforded 9.9 g (97%) of Diethyl 2-(tetrahydrofuran-2-yl)malonate as a colorless liquid which was used in the next step without additional purification.

$^1$H NMR (CDCl$_3$, 400 MHz): δ 4.48-4.40 (m, 1H), 4.25-4.15 (m, 4H), 3.87-3.71 (m, 2H), 2.19-2.06 (m, 1H), 1.94-1.86 (m, 2H), 1.76-1.65 (m, 1H), 1.27-1.22 (m, 6H).

1,3-Dimethoxy-2-(2-tetrahydrofuryl)propane

To a suspension of lithium aluminum hydride (40.6 g, 1.07 mol) in anhydrous diethyl ether (2 L) Diethyl 2-(tetrahydrofuran-2-yl)malonate (54.0 g, 235 mmol) was added portion-wise at 0° C. The obtained solution was stirred for 2 h at room temperature and quenched carefully with 150 mL of water. The obtained suspension was filtered through a pad of Celite 503, and the solvent was removed in vacuum. The procedure yielded 12.8 g of crude 2-(Tetrahydrofuran-2-yl)propane-1,3-diol as a yellow oil which was used in the next step without additional purification.

To a suspension of sodium hydride (60 wt % in mineral oil, 10.6 g, 263 mmol) in anhydrous THF (300 mL) crude 2-(Tetrahydrofuran-2-yl)propane-1,3-diol (12.8 g) was added portion-wise at 0° C. The obtained mixture was stirred for 30 min at room temperature and methyl iodide (49.8 g, 351 mmol) was added at 0° C. The obtained mixture was stirred for 3 h at room temperature and quenched carefully with 200 mL of water. The crude product was extracted with 3×200 mL of diethyl ether. The combined extract was dried over $Na_2SO_4$ and the volatiles evaporated to dryness in vacuum. Fractional distillation of the crude product provided 11.0 g (71%) of a colorless oil (b.p. 85-90° C./15 mbar) of 1,3-Dimethoxy-2-(2-tetrahydrofuryl)propane, alternatively named 2-[2-Methoxy-1-(methoxymethyl) ethyl]tetrahydrofuran or 2-(1,3-dimethoxypropan-2-yl)tetrahydrofuran).

$^1$H NMR (CDCl$_3$, 400 MHz): δ 3.82-3.72 (m, 2H), 3.68-3.61 (m, 1H), 3.49-3.38 (m, 2H), 3.36 (d, J=5.5 Hz, 2H), 3.26 (s, 3H), 3.25 (s, 3H), 1.95-1.75 (m, 4H), 1.63-1.52 (m, 1H).

$^{13}$C{$^1$H} NMR (CDCl$_3$, 100 MHz): δ 77.8, 71.1, 70.7, 67.5, 58.8, 44.2, 29.4, 25.6.

ID5: 1,3-Dimethoxy-2-(2-furyl)propane (DMFP)

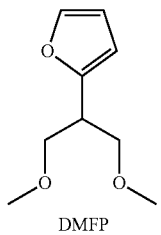

DMFP

Diethyl 2-furylmalonate

A mixture of furan (102 g, 1.50 mol), Diethyl malonate (432 g, 2.70 mol), methanol (2700 mL), water (300 mL), and of Ce(SO$_4$)$_2$·4H$_2$O (242 g, 0.60 mol) was stirred under an argon atmosphere for 12 h at room temperature. The obtained suspension was filtered through a pad of Celite 503. The filtrate was poured into 2 L of water. The crude product was extracted with 3×500 mL of dichloromethane. The combined extract was dried over Na$_2$SO$_4$ and the volatiles evaporated to dryness. Fractional distillation of the residue provided 55.6 g (82%) of Diethyl 2-furylmalonate as a yellow oil (b.p. 95-100° C./2 mbar).

$^1$H NMR (CDCl$_3$, 400 MHz): δ 7.40 (br.s, 1H), 6.41 (m, 2H), 4.76 (s, 1H), 4.24 (q, 4H, J=7.0 Hz), 1.28 (t, 6H, J=7.0 Hz).

2-(2-Furyl)propane-1,3-diol

To a suspension of lithium aluminum hydride (53.8 g, 1.42 mol) in anhydrous diethyl ether (1800 mL) Diethyl 2-furylmalonate (80.0 g, 354 mmol) was added portion-wise at 0° C. The obtained solution was stirred for 2 h at room temperature and quenched carefully with 200 mL of water. The obtained suspension was filtered through a pad of Celite 503. The filtrate was evaporated to dryness. Fractional distillation of the residue yielded 5.8 g (12%) of 2-(2-Furyl) propane-1,3-diol as a colorless oil (b.p. 95° C./2 mbar).

$^1$H NMR (CDCl$_3$, 400 MHz): δ 7.34 (dd, 1H, J=1.7 Hz, J=0.7 Hz), 6.20 (dd, 1H, J=3.3 Hz, J=1.9 Hz), 6.15 (d, 1H, J=3.3 Hz), 3.55 (d, 4H, J=6.5 Hz), 3.26 (qv, 1H, J=6.5 Hz), 2.25 (br.s, 2H).

1,3-Dimethoxy-2-(2-furyl)propane

To a suspension of sodium hydride (60 wt % in mineral oil, 4.9 g, 123 mmol) in anhydrous THF (250 mL) 2-(2-Furyl)propane-1,3-diol (5.8 g, 40.8 mmol) was added portion-wise at 0° C. The obtained mixture was stirred for 30 min at room temperature, cooled to 0° C. and methyl iodide (10.2 g, 163 mmol) was added. The obtained mixture was stirred for 3 h at room temperature and quenched carefully with 100 mL of water. The crude product was extracted with 3×100 mL of diethyl ether. The combined extract was dried over Na$_2$SO$_4$ and the volatiles evaporated to dryness. Fractional distillation of the residue yielded 4.9 g (71%) of a colorless oil (b.p. 67° C./40 mbar) of 1,3-Dimethoxy-2-(2-furyl)propane, alternatively named 2-[2-Methoxy-1-(methoxymethyl)ethyl]furan or 2-(1,3-dimethoxypropan-2-yl)furan.

$^1$H NMR (CDCl$_3$, 400 MHz): δ 7.32 (dd, 1H, J=1.7 Hz, J=0.7 Hz), 6.29 (dd, 1H, J=3.1 Hz, J=1.9 Hz), 6.13 (d, 1H, J=3.2 Hz), 3.63 (d, 4H, J=6.2 Hz), 3.33 (s, 6H), 3.26 (qv, 1H, J=6.2 Hz).

$^{13}$C{$^1$H} NMR (CDCl$_3$, 100 MHz): δ 154.3, 141.2, 110.2, 105.9, 72.0, 59.0, 40.0.

ID6: 1,3-Dimethoxy-2-methyl-2-(2-tetrahydrofuryl) propane (DMMTHFP)

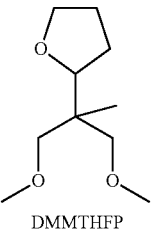

DMMTHFP

A mixture of 2-(1,3-Dimethoxy-2-methylpropan-2-yl) furan (18.4 g, 0.100 mmol), 5% Pd/C (900 mg), and isopropanol (20 mL) was placed into a 200 mL autoclave which was purged with argon and pressurized with hydrogen (70 bar). This mixture was then stirred for 1 h at room temperature. After depressurization, the obtained mixture was diluted with dichloromethane and filtered through a pad of Celite 503. The filtrate volatiles were evaporated in vacuum and the residue was passed through a pad of silica gel 60 (40-63 um, eluent: hexane/ethyl acetate=3: 1, vol.). The solvent was removed in vacuum. This procedure afforded 14.5 g (77%) of 1,3-Dimethoxy-2-methyl-2-(2-tetrahydrofuryl)propane, alternatively named 2-(1,3-dimethoxy-2-methylpropan-2-yl)tetrahydrofuran, as a colorless liquid.

$^1$H NMR (CDCl$_3$, 400 MHz): δ 3.82-3.68 (m, 3H), 3.37-3.27 (m, 2H), 3.31 (s, 3H), 3.29 (s, 3H), 3.26-3.18 (m, 2H), 1.86-1.66 (m, 4H), 0.83 (s, 3H).

$^{13}$C{$^1$H} NMR (CDCl$_3$, 100 MHz): δ 81.0, 75.7, 75.6, 68.1, 59.3, 42.1, 26.1, 26.0, 14.7.

ID7: 1,3-Dimethoxy-2-methyl-2-(2-furyl)propane
2-(1,3-dimethoxy-2-methylpropan-2-yl)furan
(DMMFP)

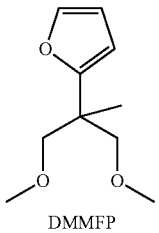

DMMFP

Diethyl 2-furyl(methyl)malonate

A mixture of furan (68 g, 1.00 mol), Diethyl methyl malonate (313 g, 1.80 mol), methanol (1800 mL), water (200 mL), and $Ce(SO_4)_2 \cdot 4H_2O$ (162 g, 0.40 mol) was stirred under an argon atmosphere for 12 h at room temperature. The obtained suspension was filtered through a pad of Celite 503. The filtrate was poured into 2 L of water. The crude product was extracted with 3×300 mL of dichloromethane. The combined extract was dried over $Na_2SO_4$ and the volatiles evaporated to dryness. Fractional distillation of the residue yielded 34.4 g (72%) of Diethyl 2-furyl(methyl)malonate as a yellow oil (b.p. 97-100° C./2 mbar).

$^1$H NMR ($CDCl_3$, 400 MHz): δ 7.38 (s, 1H), 6.34 (s, 2H), 4.22 (q, 4H, J=7.1 Hz), 1.81 (s, 3H), 1.24 (t, 6H, J=7.1 Hz)

2-(2-Furyl)-2-methylpropane-1,3-diol

To a suspension of lithium aluminum hydride (43.5 g, 1.15 mol) in anhydrous diethyl ether (2 l) Diethyl 2-furyl(methyl)malonate (68.7 g, 354 mmol) was added portionwise at 0° C. The obtained solution was stirred for 2 h at room temperature and then quenched carefully with 165 mL of water. The obtained suspension was filtered through a pad of Celite 503. The filtrate volatiles were evaporated to dryness. The residue was diluted with 100 mL diethyl ether and the precipitate was filtered off. This procedure afforded 26.0 g (58%) of 2-(2-Furyl)-2-methylpropane-1,3-diol as a white solid.

$^1$H NMR ($CDCl_3$, 400 MHz): δ 7.38-7.41 (m, 1H), 6.36 (dd, 1H, J=3.2 Hz, J=1.8 Hz), 6.22 (d, 1H, J=3.2 Hz), 3.86-3.92 (m, 2H), 3.76-3.80 (m, 2H), 2.25 (br.s, 2H), 1.28 (s, 3H)

1,3-Dimethoxy-2-methyl-2-(2-furyl)propane

To a suspension of sodium hydride (60 wt % in mineral oil, 13.0 g, 327 mmol) in anhydrous THF (400 mL) 2-(2-Furyl)-2-methyl-propane-1,3-diol (17.0 g, 109 mmol) was added portion-wise at 0° C. The obtained mixture was stirred for 30 min at room temperature, cooled to 0° C. and methyl iodide (20.5 mL, 327 mmol) was added. The obtained mixture was stirred for 3 h at room temperature and quenched carefully with 200 mL of water. The crude product was extracted with 3×200 mL of diethyl ether. The combined extract was dried over $Na_2SO_4$ and the volatiles evaporated to dryness. Fractional distillation of the residue yielded 18.9 g (94%) of 1,3-Dimethoxy-2-methyl-2-(2-furyl)propane, alternatively named 2-(1,3-Dimethoxy-2-methylpropan-2-yl)furan, as colorless oil (b.p. 72° C./40 mbar).

$^1$H NMR ($CDCl_3$, 400 MHz): δ 7.34-7.36 (m, 1H), 6.32 (dd, 1H, J=3.1 Hz, J=1.9 Hz), 6.13 (d, 1H, J=3.2 Hz), 3.51-3.58 (m, 4H), 3.31 (s, 6H), 1.28 (s, 3H).

$^{13}$C{$^1$H} NMR ($CDCl_3$, 100 MHz): δ 158.2, 141.0, 110.0, 105.0, 76.5, 59.4, 41.9, 19.1.

ID8: (3-Methoxypropyl)dimethylamine (MPDMA)

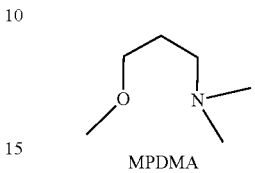

MPDMA (3-Methoxypropyl)dimethylamine (CAS 20650-07-1), alternatively named 3-Methoxy-N,N-dimethylpropan-1-amine, was acquired from UORSY.

Inventive and Comparative Catalyst Components

Inventive catalyst components (IC2-IC8), a reference catalyst component (RC1) and comparative catalyst components (CC1-a and CC1-b) were prepared according to the procedure of the Reference Example 2 of WO2016/124676 A1, but using inventive donors (ID2-ID8), reference donor (RD1) and comparative donor (CD1), respectively. Summary of donors used in catalyst component examples is disclosed in Table 1.

Comparative catalyst component CC2 is a catalyst commercially available from Grace under the trade name Lynx 200.

Raw Materials

The 10 wt % TEA (triethylaluminium) stock solutions in heptane were prepared by dilution of 100 wt % TEA-S from Chemtura.

$MgCl_2 \cdot 3EtOH$ carriers were received from Grace.

$TiCl_4$ was supplied by Aldrich (metallic impurities <1000 ppm, Metals analysis >99.9%).

General Procedure for Catalyst Component Preparation

In an inert atmosphere glovebox a dry 100 mL, 4-neck round-bottom flask, equipped with two rubber septa, a thermometer and a mechanical stirrer, was charged with 3.1 mmol of a desired INTERNAL DONOR (INTERNAL DONOR and INTERNAL DONOR/Mg loading ratio are indicated in Tables 1 and 2) dissolved in 40 mL of heptane and with 7.01 g (30 mmol of Mg) of granular 17 μm ($D_{v,0.5}$) $MgCl_2 \cdot 2.93EtOH$ carrier. The flask was removed from the glovebox, a nitrogen inlet and an outlet were connected. The flask was placed in a cooling bath and tempered at 0° C. for approximately 10 min at 250 rpm. Triethylaluminium 10 wt % solution in heptane (107.55 g, 94.2 mmol Al; Al/EtOH=1.07 mol/mol) was added drop-wise to the stirred suspension within 1 h, keeping the reaction mixture temperature below 0° C. The obtained suspension was heated to 80° C. within 20 min and kept at this temperature for further 30 min at 250 rpm. The suspension was left to settle for 5 min at 80° C. and the supernatant was removed using a cannula. The obtained pre-treated support material was washed twice with 70 mL of toluene at room temperature (adding toluene, stirring at 250 rpm for 15-120 min, settling for 5 min and siphoning the liquid phase off).

At room temperature, 70 mL of toluene was added to the pre-treated support material. To this suspension stirred at 250 rpm, neat $TiCl_4$ (3.31 mL, 30 mmol; Ti/Mg=1.0 mol/mol) was added drop-wise and the reaction mixture temperature was maintained between 25-35° C. The obtained suspension was heated to 90° C. within 20 min and stirred at this temperature for further 60 min at 250 rpm. The suspension was left to settle for 5 min at 90° C. and the supernatant was removed using a cannula. The obtained catalyst was washed twice with 70 mL of toluene at 90° C. and once with 70 mL of heptane at room temperature (each wash involving adding toluene or heptane, stirring at 250 rpm for 15 min, settling for 5 min and siphoning the liquid phase off). The catalyst component was dried in vacuo at 70° C. for 30 min.

TABLE 1

Summary of donors used in catalyst components CC1-a-CC1-b, reference component RC1, and IC2-IC8

| Examples | Catalyst component | Internal Donor | Internal Donor short name |
|---|---|---|---|
| Comparative | CC1-a | CD1 | DMMF |
| Comparative | CC1-b | CD1 | DMMF |
| Reference | RC1 | RD1 | DMP |
| Inventive | IC2 | ID2 | DMMP |
| Inventive | IC3 | ID3 | DMDMP |
| Inventive | IC4 | ID4 | DMTHFP |
| Inventive | IC5 | ID5 | DMFP |
| Inventive | IC6 | ID6 | DMMTHFP |
| Inventive | IC7 | ID7 | DMMFP |
| Inventive | IC8 | ID8 | MPDMA |

Comparative Examples

CC1-a Preparation

CC1-a was prepared using the above General Procedure, with a difference that 0.778 g (3.1 mmol) of CD1 (DMMF) were used as internal donor (ID/Mg=0.102).

2.3 g (57.4% yield, Mg-basis) of CC1-a were isolated.

CC1-b Preparation

CC1-b was prepared using the above General Procedure, with a difference that 1.038 g (4.1 mmol) of CD1 (DMMF) were used as internal donor (ID/Mg=0.136).

2.8 g (64.5% yield, Mg-basis) of CC1-b were isolated.

Reference Catalyst Example

RC1 Preparation

RC1 was prepared using the above General Procedure, with a difference that 0.159 g (1.5 mmol) of ID1 (DMP) were used as internal donor (ID/Mg=0.051).

2.6 g (67.7% yield, Mg-basis) of IC1 were isolated.

Inventive Catalyst Examples

IC2 Preparation

IC2 was prepared using the above General Procedure, with a difference that 0.24 g (2.0 mmol) of ID2 (DMMP) were used as internal donor (ID/Mg=0.068).

2.8 g (75.3% yield, Mg-basis) of IC2 were isolated.

IC3 Preparation

IC3 was prepared using the above General Procedure, with a difference that 0.270 g (2.0 mmol) of ID3 (DMDMP) were used as internal donor (ID/Mg=0.068).

2.4 g (61.5% yield, Mg-basis) of IC3 were isolated.

IC4 Preparation

IC4 was prepared using the above General Procedure, with a difference that 0.36 g (2.0 mmol) of ID4 (DMTHFP) were used as internal donor (ID/Mg=0.068).

4.0 g (78.4% yield, Mg-basis) of IC4 were isolated.

IC5 Preparation

IC5 was prepared using the above General Procedure, with a difference that 0.52 g (3.1 mmol) of ID5 (DMFP) were used as internal donor (ID/Mg=0.102).

3.5 g (80.6% yield, Mg-basis) of IC5 were isolated.

IC6 Preparation

IC6 was prepared using the above General Procedure, with a difference that 0.38 g (2.0 mmol) of ID6 (DMMTHFP) were used as internal donor (ID/Mg=0.068).

4.3 g (95.5% yield, Mg-basis) of IC6 were isolated.

IC7 Preparation

IC7 was prepared using the above General Procedure, with a difference that 0.38 g (2.0 mmol) of ID7 (DMMFP) were used as internal donor (ID/Mg=0.068).

3.3 g (82.4% yield, Mg-basis) of IC7 were isolated.

IC8 Preparation 108 was prepared using the above General Procedure, with a difference that 0.36 g (3.1 mmol) of ID8 (MPDMA) were used as internal donor (ID/Mg=0.102).

4.3 g (89.1% yield, Mg-basis) of IC8 were isolated.

TABLE 2

Summary of properties of catalyst components CC1-a, CC1-b, RC1 and IC2-IC8.

| Catalyst component | Internal donor (ID) | ID/Mg loading ratio, mol/mol | Ti, wt % | Mg, wt % | Al, wt % | Cl, wt % | Volatiles, wt % | Ti(IV) proportion, % | Mg/Ti ratio, mol/mol | Mg/Al ratio, mol/mol |
|---|---|---|---|---|---|---|---|---|---|---|
| CC1-a | DMMF | 0.102 | 3.54 | 18.2 | 0.23 | 56.3 | 4.7 | 40.0 | 10.13 | 87.85 |
| CC1-b | DMMF | 0.136 | 4.00 | 16.8 | 0.37 | 55.2 | 5.4 | 26.2 | 8.27 | 50.41 |
| RC1 | DMP | 0.051 | 4.94 | 19.0 | 0.42 | 64.6 | 4.1 | 18.3 | 7.57 | 50.22 |
| IC2 | DMMP | 0.068 | 4.45 | 19.6 | 0.45 | 63.5 | 3.4 | 22.0 | 8.67 | 48.35 |
| IC3 | DMDMP | 0.068 | 4.07 | 18.7 | 0.37 | 65.0 | 5.7 | 22.8 | 9.05 | 56.11 |
| IC4 | DMTHFP | 0.068 | 7.35 | 14.3 | 1.18 | 60.2 | 5.3 | 84.1 | 3.83 | 13.45 |
| IC5 | DMFP | 0.102 | 4.56 | 16.9 | 0.95 | 59.1 | 6.4 | 17.4 | 7.30 | 19.75 |
| IC6 | DMMTHFP | 0.068 | 6.88 | 16.2 | 1.00 | 57.8 | 7.5 | 22.1 | 4.64 | 17.98 |
| IC7 | DMMFP | 0.068 | 5.00 | 18.2 | 0.82 | 60.7 | 2.9 | 23.7 | 7.17 | 24.64 |
| IC8 | MPDMA | 0.102 | 8.96 | 15.0 | 0.99 | 66.4 | 5.7 | 6.8 | 3.30 | 16.82 |

Bench-Scale Ethylene Copolymerization with 1-Butene

The inventive catalyst components (102-108), the reference catalyst component (RC1) and the comparative catalyst components (CC1-a, CC1-b and CC2) were tested in ethylene copolymerization with 1-butene (IE2-IE8, RE1, CE1-a, CE1-b and CE2-a). Triethylaluminum (TEA) was used as a cocatalyst with an Al/Ti molar ratio of 15. The polymerization reaction was carried out in a 3 L bench-scale reactor in accordance with the following procedure:

An empty 3 L bench-scale reactor was charged with 70 mL of 1-butene at 20° C. and stirred at 200 rpm. Then 1250 mL of propane was added to the reactor as a polymerization medium, followed by the addition of hydrogen gas (0.40 bar). The reactor was heated to 85° C. and ethylene (3.7 bar) was added batch-wise. The reactor pressure was kept at 0.2 bar of overpressure and stirring speed was increased to 550 rpm. The catalyst component and the cocatalyst were added together (a few seconds of pre-contact between catalyst component and TEA) to the reactor with additional 100 mL of propane. The total reactor pressure was maintained at 37.8 bar by continuous ethylene feed. The polymerization was stopped after 60 min by venting off the monomers and $H_2$. The obtained polymer was left to dry in a fume hood overnight before weighing.

Additionally, the comparative catalyst component CC2 was tested in copolymerization also with 55 mL of 1-butene and 0.40 bar of hydrogen gas (CE2-b) and with 40 mL of 1-butene and 0.75 bar of hydrogen gas (CE2-c).

Polymerization Results

The results of the polymerization reactions are shown in Table 3. The activity of the catalysts was calculated based on catalyst component loading amount and the amount of polymer produced in one hour.

TABLE 3

Summary of polymerization results for comparative examples CE1-a, CE1-b, CE2-a-CE2-c, reference example RE1 and inventive examples IE2-IE8.

| Polymerization Example | Catalyst component | Activity, kg/(g * h) | 1-Butene content, wt % | $MFR_{21}$ g/10 min | $M_w$, g/mol | PDI | $T_M$ ° C. |
|---|---|---|---|---|---|---|---|
| CE1-a | CC1-a | 19.2 | 4.4 | 3.7 | 211500 | 4.61 | 122.85 |
| CE1-b | CC1-b | 17.3 | 4.8 | 3.9 | 215500 | 4.52 | 123.16 |
| CE2-a | CC2 | 55 | 6.2 | 5.3 | 200000 | 4.80 | 122.4 |
| CE2-b | CC2 | 54 | 4.8 | 3.0 | 220000 | 4.71 | 123.4 |
| CE2-c | CC2 | 58 | 3.9 | 8.3 | 160000 | 4.64 | 124.9 |
| RE1 | RC1 | 29.1 | 4.8 | 2.9 | 228000 | 4.23 | 122.27 |
| IE2 | IC2 | 27.4 | 4.4 | 1.5 | 260500 | 4.01 | 121.97 |
| IE3 | IC3 | 22.1 | 5.6 | 3.1 | 217500 | 4.46 | 121.80 |
| IE4 | IC4 | 19.0 | 4.9 | 2.8 | 236000 | 4.47 | 123.09 |
| IE5 | IC5 | 14.0 | 4.2 | 1.2 | 276500 | 3.99 | 121.61 |
| IE6 | IC6 | 21.2 | 4.6 | 2.9 | 224000 | 4.42 | 122.57 |
| IE7 | IC7 | 20.4 | 4.7 | 2.2 | 243500 | 4.32 | 122.08 |
| IE8 | IC8 | 21.4 | 4.3 | 4.1 | 198000 | 3.92 | 123.26 |

As can be seen from the results and as also shown in FIG. 1, inventive examples (IE2-IE8) and reference example RE1 exhibit a narrower MWD (described by PDI) than comparative examples CE1 and CE2. While IE2-IE7 and reference example RE1 possesses similar or higher average $M_w$ and narrower MWD than CE1-CE2, IE8 possesses a similar average $M_w$ with a much narrower MWD compared to CE1-CE2.

Further (as shown in FIG. 2), all inventive examples (IE2-IE8) and reference example RE1 have a lower melting temperature Tm at a given comonomer content than comparative examples CE2 and a lower or similar melting temperature at a given comonomer content than comparative examples CE1.

In addition, as shown by the examples and in FIG. 3, all inventive examples (IE2-IE8) and reference example RE1 demonstrate an activity level which is similar to the comparative examples CE1 with a similar or higher $M_w$ capability.

Moreover, in all inventive examples (IE2-IE8) and reference example RE1 the desired balance of properties is achieved with similar or lower ID/Mg loading ratios.

To summarize the findings, while IE2 and IE5 have the highest $M_w$ combined with very narrow MWD and with lowest melting temperature at a given comonomer content, IE8 has lowest $M_w$ combined with narrowest MWD and with moderate melting temperature at a given comonomer content. Thus, the inventive internal donors allow for "tailoring" of the properties of the produced polymers while maintaining catalyst productivity at acceptably high level.

The invention claimed is:

1. A compound of formula (I-c)

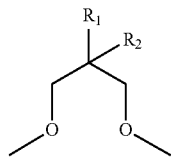

(I-c)

wherein
$R_1$ is selected from a group consisting of tetrahydrofuryl and furyl; and
$R_2$ is selected from H and methyl.

2. A Ziegler-Natta catalyst component for olefin polymerization, comprising
an internal donor selected from compounds of formula (I)

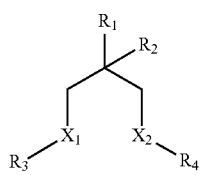

(I)

wherein
X₁ and X₂ are each independently selected from O and N(R₅);
R₁ is an oxygen-containing heterocyclic ring;
R₂ is selected from H and methyl;
R₃ and R₄ are independently selected from $C_{1-4}$-alkyl;
R₅ is selected from a group consisting of H, a linear $C_{1-8}$-alkyl group, a branched $C_{1-8}$-alkyl group, and a cyclic $C_{1-8}$-alkyl group.

3. The Ziegler-Natta catalyst component according to claim 2, wherein the compound of formula (I) is selected from compounds of formula (I-a)

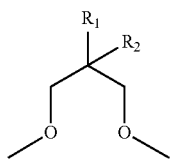

(I-a)

wherein
R₁ is an oxygen-containing heterocyclic ring; and
R₂ is selected from H and methyl.

4. The Ziegler-Natta catalyst component according to claim 2, further comprising:
   (ii) a compound of a transition metal of Group 4 to 6 of the Periodic Table (IUPAC, Nomenclature of Inorganic Chemistry, 2005);
   (iii) a compound of a metal of Group 1 to 3 of the Periodic Table (IUPAC, 2005); and
   (iv) optionally, a compound of an element of Group 13 of the Periodic Table (IUPAC, 2005).

5. The Ziegler-Natta catalyst component according to claim 2, wherein the Ziegler-Natta catalyst component comprises
   (ii) a Group 4 to 6 metal content (determined by ICP Analysis) in the range of 1.0 wt % to 15.0 wt % of the total weight of the Ziegler-Natta catalyst component;
   (iii) a Group 1 to 3 content (determined by ICP Analysis) in the range of 5.0 wt % to 30.0 wt % of the total weight of the Ziegler-Natta catalyst component;
   (iv) a Group 13 element content (determined by ICP Analysis) in the range of 0.0 wt % to 3.0 wt % of the total weight of the Ziegler-Natta catalyst component.

6. The Ziegler-Natta catalyst component according to claim 2, wherein the Ziegler-Natta catalyst component is obtained by a method comprising:
   (M-a) providing a solid support;
   (M-b) pre-treating the solid support of step (M-a) with a compound of Group 13 element;
   (M-c) treating the pre-treated solid support of step (M-b) with a compound of a transition metal of Group 4 to 6; and
   (M-d) recovering the Ziegler-Natta catalyst component;
wherein the solid support is contacted with an internal donor selected from compounds of formula (I) or mixtures therefrom before treating the solid support in step (M-c).

7. A method for producing a Ziegler-Natta catalyst component, comprising adding an internal donor selected from compounds of formula (I)

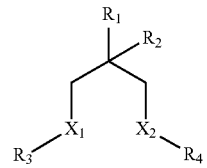

(I)

wherein
X₁ and X₂ are each independently selected from O and N(R₅);
R₁ is an oxygen-containing heterocyclic ring;
R₂ is selected from H and methyl;
R₃ and R₄ are independently selected from $C_{1-4}$-alkyl;
R₅ is selected from a group consisting of H, a linear $C_{1-8}$-alky group, a branched $C_{1-8}$-alkyl group, and a cyclic $C_{1-8}$-alkyl group
to a process of preparing the Ziegler-Natta catalyst component.

8. The method according to claim 7, wherein the method comprises:
   (M-a) providing a solid support;
   (M-b) pre-treating the solid support of step (M-a) with a compound of Group 13 element;
   (M-c) treating the pre-treated solid support of step (M-b) with a transition metal compound of Group 4 to 6;
   (M-d) recovering the Ziegler-Natta catalyst component;
wherein the solid support is contacted with an internal donor selected from compounds of formula (I) or mixtures therefrom before treating the solid support in step (M-c).

9. A method for producing a Ziegler-Natta catalyst component, comprising adding an internal donor selected from compounds of formula (I)

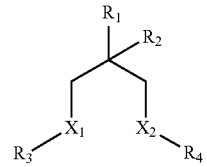

(I)

wherein
X₁ and X₂ are each independently selected from O and N(R₅);
R₁ is an oxygen-containing heterocyclic ring;
R₂ is selected from H and methyl;
R₃ and R₄ are independently selected from $C_{1-4}$-alkyl;
R₅ is selected from a group consisting of H, a linear $C_{1-8}$-alkyl group, a branched $C_{1-8}$-alkyl group, and a cyclic $C_{1-8}$-alkyl group
to a process of preparing the Ziegler-Natta component;
wherein the method comprises:
   (M-a) providing a solid support;
   (M-b) pre-treating the solid support of step (M-a) with a compound of Group 3 element;
   (M-c) treating the pre-treated solid support of step (M-b) with a transition metal compound of Group 4 to 6;
   (M-d) recovering the Ziegler-Natta catalyst component;

wherein the solid support is contacted with an internal donor selected from compounds of formula (I) or mixtures therefrom before treating the solid support in step (M-c), and wherein the Ziegler-Natta catalyst component is the Ziegler-Natta catalyst component as defined in claim 4.

10. A Ziegler-Natta catalyst for olefin polymerization comprising:
(A) the Ziegler-Natta catalyst component as defined in claim 4 or prepared by the method as defined in claim 7;
(B) a cocatalyst selected from compounds of element of Group 13 of the Periodic Table (IUPAC, 2005); and
(C) optionally, an external donor.

11. A method of olefin polymerization, comprising:
introducing into a polymerization reactor a Ziegler-Natta catalyst comprising the Ziegler-Natta catalyst component according to claim 2 comprising an internal donor selected from compounds of formula (I)

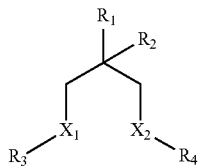

(I)

wherein
$X_1$ and $X_2$ are each independently selected from O and $N(R_5)$;
$R_1$ is an oxygen-containing heterocyclic ring;
$R_2$ is selected from H and methyl;
$R_3$ and $R_4$ are independently selected from $C_{1-4}$-alkyl;
$R_5$ is selected from a group consisting of H, a linear $C_{1-8}$-alkyl group, a branched $C_{1-8}$-alkyl group, and a cyclic $C_{1-8}$-alkyl group.

12. A method of olefin polymerization, comprising:
introducing into a polymerization reactor a Ziegler-Natta catalyst component prepared by the method as defined in claim 7 comprising an internal donor selected from compounds of formula (I)

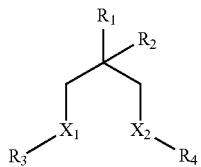

(I)

wherein
$X_1$ and $X_2$ are each independently selected from O and $N(R_5)$;
$R_1$ is an oxygen-containing heterocyclic ring;
$R_2$ is selected from H and methyl;
$R_3$ and $R_4$ are independently selected from $C_{1-4}$-alkyl;
$R_5$ is selected from a group consisting of H, a linear $C_{1-8}$-alkyl group, a branched $C_{1-8}$-alkyl group and a cyclic $C_{1-8}$-alkyl group.

13. A process for producing ethylene homo- or copolymers, comprising:
(P-a) introducing the Ziegler-Natta catalyst component according to claim 2 into a polymerization reactor;

(P-b) introducing a cocatalyst capable of activating the said Ziegler-Natta catalyst component into the polymerization reactor;
(P-c) introducing ethylene, optionally $C_3$-$C_{20}$ α-olefin comonomers, and optionally hydrogen into the polymerization reactor; and
(P-d) maintaining said polymerization reactor in such conditions as to produce an ethylene homo- or copolymer.

14. The process according to claim 13, wherein olefin polymerization is accomplished in a multi-stage polymerization process comprising at least one gas phase reactor for producing olefin polymers.

15. The process according to claim 13, wherein olefin polymerization is accomplished in a multi-stage polymerization process comprising at least one slurry reactor and one gas phase reactor.

16. A Ziegler-Natta catalyst component for olefin polymerization, comprising
an internal donor selected from compounds of formula (I)

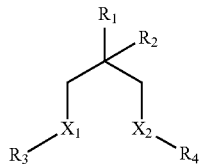

(I)

wherein
$X_1$ and $X_2$ are each independently selected from O and $N(R_5)$;
$R_1$ is selected from a group consisting of H, $C_{1-3}$-alkyl, and oxygen-containing heterocyclic ring;
$R_2$ is selected from H and methyl, with the provisio that only one of $R_1$ and $R_2$ may be H, if $X_1$ and $X_2$ are O;
$R_3$ and $R_4$ are independently selected from $C_{1-4}$-alkyl;
$R_5$ is selected from a group consisting of H, a linear $C_{1-8}$-alkyl group, a branched $C_{1-8}$-alkyl group and a cyclic $C_{1-8}$-alkyl group,
wherein the Ziegler-Natta catalyst component is obtained by a method comprising:
(M-a) providing a solid support;
(M-b) pre-treating the solid support of step (M-a) with a compound of Group 13 element;
(M-c) treating the pre-treated solid support of step (M-b) with a compound of a transition metal of Group 4 to 6; and
(M-d) recovering the Ziegler-Natta catalyst component;
wherein the solid support is contacted with an internal donor selected from compounds of formula (I) or mixtures therefrom before treating the solid support in step (M-c).

17. A method for producing a Ziegler-Natta catalyst component, comprising adding an internal donor selected from compounds of formula (I)

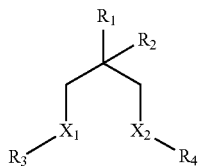

(I)

wherein $X_1$ and $X_2$ are each independently selected from O and $N(R_5)$;

$R_1$ is selected from a group consisting of H, $C_{1-3}$-alkyl, and oxygen-containing heterocyclic ring;

$R_2$ is selected from H and methyl, with the proviso that only one of $R_1$ and $R_2$ may be H, if $X_1$ and $X_2$ are O;

$R_3$ and $R_4$ are independently selected from $C_{1-4}$-alkyl;

$R_5$ is selected from a group consisting of H, a linear $C_{1-8}$-alkyl group, a branched $C_{1-8}$-alkyl group and a cyclic $C_{1-8}$-alkyl group to a process of preparing the Ziegler-Natta catalyst component, wherein the method comprises:

(M-a) providing a solid support;

(M-b) pre-treating the solid support of step (M-a) with a compound of Group 13 element;

(M-c) treating the pre-treated solid support of step (M-b) with a transition metal compound of Group 4 to 6;

(M-d) recovering the Ziegler-Natta catalyst component;

wherein the solid support is contacted with an internal donor selected from compounds of formula (I) or mixtures therefrom before treating the solid support in step (M-c).

* * * * *